United States Patent [19]

Yokoya et al.

[11] Patent Number: 5,102,760
[45] Date of Patent: Apr. 7, 1992

[54] ELECTROPHOTOGRAPHIC PHOTORECEPTOR AND ELECTROPHOTOGRAPHIC PRINTING PLATE PRECURSOR COMPRISING PHTHALOCYANINE PIGMENT AND THIOBARBITURIC ACID DERIVATIVE

[75] Inventors: Hiroaki Yokoya; Hiromichi Tachikawa; Syu Watarai; Syunichi Kondo; Seiji Horie, all of Kanagawa, Japan

[73] Assignee: Fuji Photo Film Co., Ltd., Kanagawa, Japan

[21] Appl. No.: 584,027

[22] Filed: Sep. 18, 1990

[30] Foreign Application Priority Data

Sep. 18, 1989 [JP] Japan .................. 1-240964
Sep. 26, 1989 [JP] Japan .................. 1-250005

[51] Int. Cl.⁵ ............................................. G03G 5/04
[52] U.S. Cl. .......................... 430/78; 430/83; 430/49
[58] Field of Search .................... 430/78, 83, 49

[56] References Cited

U.S. PATENT DOCUMENTS 4,500,622  2/1985  Horie et al. ............ 430/83 X

*Primary Examiner*—David Welsh
*Attorney, Agent, or Firm*—Sughrue, Mion, Zinn, Macpeak & Seas

[57] ABSTRACT

A novel electrophotographic photoreceptor for copiers or photoprinters is provided comprising a photoconducting layer provided on an electrically conductive support, wherein said photoconducting layer comprises a phthalocyanine pigment and at least one compound represented by the general formula (I) or (II):

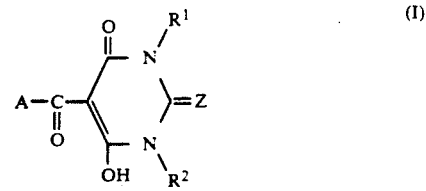

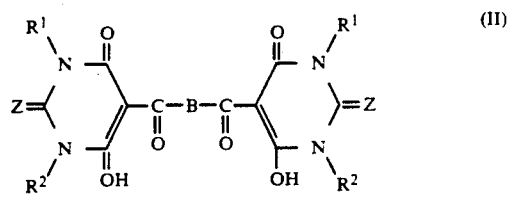

wherein Z represents a sulfur atom or oxygen atom; $R^1$ and $R^2$ may be the same or different and each represents a hydrogen atom, alkyl group, aryl group or aralkyl group; A represents an alkyl group, aryl group, aralkyl group or monovalent heterocyclic group; and B represents an alkylene group, arylene group, polymethylene group or aralkylene group.

A novel electrophotographic printing plate precursor is also provided which comprises a photoconducting layer containing at least a photoconducting pigment and a binder resin on an electrically conductive support and is adapted to form a printing plate in an electrophotographic process comprising forming a toner image, and then removing said photoconducting layer from the non-image portions except said toner image portions, characterized in that said photoconducting pigment is a phthalocyanine pigment and said photoconducting layer further comprises a compound represented by the general formula [I] or [II]:

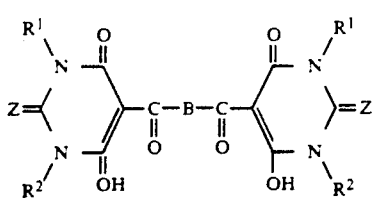

-continued (II)

wherein Z represents a sulfur atom or oxygen atom; $R^1$ and $R^2$ may be the same or different and each represents a hydrogen atom, alkyl group, aryl group or aralkyl group; A represents an alkyl group, aryl group, aralkyl group or monovalent heterocyclic group; and B represents an alkylene group, arylene group, polymethylene group or aralkylene group.

15 Claims, 1 Drawing Sheet

ELECTROPHOTOGRAPHIC PHOTORECEPTOR AND ELECTROPHOTOGRAPHIC PRINTING PLATE PRECURSOR COMPRISING PHTHALOCYANINE PIGMENT AND THIOBARBITURIC ACID DERIVATIVE

FIELD OF THE INVENTION

The present invention relates to a novel electrophotographic photoreceptor and electrophotographic printing plate precursor comprising a phthalocyanine pigment and a thiobarbituric acid derivative.

BACKGROUND OF THE INVENTION

A: Electrophotographic Photoreceptor

Electrophotographic photoreceptors which are sensitive to the visible light range have been developed for the purpose of application to copiers, photoprinters and the like. As such electrophotographic photoreceptors there have heretofore been widely used photoreceptors comprising as the main component an inorganic photoconducting substance such as selenium, zinc oxide and cadmium sulfide. However, such an inorganic photoreceptor does not necessarily satisfy all requirements for electrophotographic photoreceptors for copiers or the like, e.g., light sensitivity, thermal stability, moisture resistance and durability.

For example, selenium photoreceptors are subject to crystallization due to heat or stain such as fingerprint caused by touch of the hand and hence there is deterioration in the above-mentioned properties required for electrophotographic photoreceptors.

Electrophotographic photoreceptors comprising cadmium sulfide exhibit poor moisture resistance and durability. Electrophotographic photoreceptors comprising zinc oxide leave to be desired in durability such as film strength. Further, due to their toxicity, selenium and cadmium sulfide have a great restriction in production and handling.

In recent years, in order to eliminate these disadvantages of inorganic photoreceptors, photoreceptors comprising various organic substances have been developed, and some of them have been put into practical use. Examples of these organic photoreceptors include an electrophotographic photoreceptor comprising poly-N-vinyl carbazole and 2,4,7-trinitrofluorenone-9-one (U.S. Pat. No. 3,484,237), an electrophotographic photoreceptor obtained by sensitizing poly-N-vinyl carbazole with a pyrilium salt dye (JP-B-48-25658 (the term "JP-B" as used herein means an "examined Japanese patent publication"), an electrophotographic photoreceptor comprising an organic pigment as main component (JP-A-47-37543 (the term "JP-A" as used herein means an "unexamined published Japanese patent application"), and an electrophotographic photoreceptor comprising as main components a eutectic complex of a dye and a resin (JP-A-47-107785).

Although these photoreceptors give some improvements in the above-mentioned inorganic photoreceptors, they generally exhibit a low light sensitivity and are not suited for repeated use. Thus, these photoreceptors leave to be desired as electrophotographic photoreceptors.

In order to eliminate such a disadvantage, an electrophotographic photoreceptor has been proposed comprising a separate function type photoconducting layer wherein a charge-generating effect and a charge-transporting effect are separately accomplished by different substances. This kind of an electrophotographic photoreceptor has become the main subject of study. Such a separate function type electrophotographic photoreceptor is advantageous in that the range of materials to be incorporated therein can be extended, making it possible to improve the sensitivity and durability thereof. This kind of an electrophotographic photoreceptor is also advantageous in that selection can be made from a wide range of materials favorable to the formation of coating materials for forming electrophotographic photoreceptors.

As effective organic charge-generating materials to be incorporated in the charge-generating layer in such a separate function type electrophotographic photoreceptor there have been developed various organic dyes and organic pigments. For example, azo pigments, perylene pigments, polycyclic quinone pigments and squaric methine dyes having various structures have been used.

These pigments exhibit a relatively high sensitivity in a short wavelength range or middle wavelength range but exhibit a low sensitivity in a long wavelength range. Thus, these pigments can be hardly used for laser printers using a highly reliability semiconductor laser. Gallium-aluminum-arsenic light-emitting elements which are widely used as semiconductor lasers at present have an oscillation wavelength of 750 nm or more.

A phthalocyanine compound, which is one of the organic photoconducting materials, has been known to have a sensitivity range extended to the long wavelength side as compared to the above-mentioned pigments and dyes but exhibit insufficient electrophotographic properties such as sensitivity and chargeability. In order to overcome these difficulties, studies have been made to develop phthalocyanine compounds with various center metals or various crystal forms. Various crystal forms of phthalocyanine compounds have been found in the course during which an unstable $\alpha$-type phthalocyanine is converted to a $\beta$-type phthalocyanine having a crystalline stability. For example, $\epsilon$-type copper phthalocyanine, X-type metal-free phthalocyanine, and m-type titanyl phthalocyanine have been known. These phthalocyanines are sensitive to a long wavelength range but exhibit too low a sensitivity to be used for copiers or photoprinters. These phthalocyanines are also disadvantageous in that they lack potential stability or exhibit a large residual potential upon repeated use. Thus, these phthalocyanines cannot be put into practical use.

On the other hand, in an attempt to improve the sensitivity of an electrophotographic photoreceptor comprising a phthalocyanine pigment, the addition of a charge-transporting compound such as a hydrazone compound or an oxazole compound or an electron-attracting compound such as tetranitrofluorenone and trinitrofluorenone has been proposed. These approaches were found to give an effect of sensitization. However, the sensitizing effect thus attained is insufficient. These approaches are also disadvantageous in that the addition of these additives causes a drop in chargeability or a drop in potential stability or sensitivity or a rise in residual potential upon repeated use. Thus, none of these approaches could be put into practical use. Further, due to toxicity, the above-mentioned electron-attracting compounds cannot be put into practical use.

As has been described, an electrophotographic photoreceptor has been desired which is highly sensitive, particularly to light of a long wavelength of 750 nm, and exhibits a high potential stability, a small residual potential and a small drop in sensitivity upon repeated use.

B: Electrophotographic Printing Plate Precursor

Today, as lithographic offset printing plates there have been put into practical use PS plates comprising a positive light sensitive agent containing a diazo compound and a phenolic resin as main components or a negative light-sensitive agent containing an acrylic monomer or prepolymer as main component. Due to their low sensitivity, these PS plates are imagewise exposed to light with a film original which had recorded an image kept in close contact therewith. On the other hand, with the recent progress in the techniques for computer image processing storage of large capacity data and data communications, an electronic editing system has been put into practical use. In this electronic editing system, original input, correction, edit, layout and paging can be processed in a continuous computerized process, and data can be immediately outputted to remote terminal plotters via a high speed telecommunication network or satellite communications. Such an electronic editing system is in great demand particularly in the field of newspaper printing requiring rapidity. In the field where originals are stored in the form of original film, and printing plates are reproduced on these original films as necessary, too, it is likely that with the development of ultrahigh capacity recording mediums, these originals will be stored as digital data on these recording mediums.

However, little or no direct type printing plate precursors adapted to making printing plates directly from output of terminal plotters have been put into practical use. Even in offices operating with an electronic editing system, data is outputted to a silver salt system photographic film, and a PS plate is then exposed to light with this photographic film kept in close contact therewith to prepare a printing plate. This is partly because it is difficult to provide a direct type printing plate which is sufficiently sensitive to light from- a light source of the output plotter (e.g., He-Ne laser, semiconductor laser) to make a desired printing plate within a practical period of time.

As a photoreceptor which is sufficiently light-sensitive to provide a direct printing plate there can be proposed an electrophotographic photoreceptor. Many electrophotographic printing plate precursors of the type wherein non-image portions of a photoconducting layer are removed after the formation of a toner image have already been known. Examples of these electrophotographic printing plate precursors include those disclosed in JP-B-37-17162, JP-B-38-6961, JP-B-38-7758, JP-B-41-2426, and JP-B-46-39405, and JP-A-50-19509, JP-A-50-19510, JP-A-52-2437, JP-A-54-145538, JP-A-54-134632, JP-A-55-105254, JP-A-55-153948, JP-A-55-161250, JP-A-56-107246, JP-A-57-147656, and JP-A-57-161863.

JP-A-56-107246 discloses an electrophotographic printing plate precursor obtained by adding an oxazole compound as an organic photoconducting compound to a binder resin soluble in an aqueous solution of alkaline or alcohol, adding a sensitizing dye to the material, and then coating the resulting photoconducting layer on an aluminum plate. JP-A-56-146145 discloses an electrophotographic printing plate precursor comprising an oxadiazole compound as an organic photoconducting compound and a condensed polycyclic quinone pigment as charge-generating agents and an alkali-soluble carboxyl group-containing polymer. Further, JP-A-62-54266 discloses an electrophotographic printing plate precursor comprising a hydrazone compound as an organic photoconducting compound, a pigment or dye such as phthalocyanine pigment and quinacridone pigment as charge-generating agent, and a binder resin soluble in an aqueous or alcoholic solvent.

Thus, in order to use an electrophotographic photoreceptor as a printing plate, it is normally necessary to remove non-image portions with an alkaline etching solution to expose the hydrophilic surface thereof. Therefore, as a binder resin there is often used a binder resin which can be dissolved in or swell with an alkaline solvent to undergo separation. However, as compared to polycarbonate resins or the like which have been widely used as binder resins for electrophotographic photoreceptors, these resins which can be dissolved in or swell with an alkaline solvent exhibit a poor compatibility with most organic photoconducting compounds such as oxazole, hydrazone, oxadiazole and pyrazolidone. Therefore, if such an organic photoconducting compound is incorporated in a printing plate in the form of a solution, it can be separated and deposited with time. Further, due to its poor solubility in an etching solution, such an organic photoconducting compound exhibits an insufficient elutability with the etching solution at non-image portions thereof, causing stain on the white background upon printing.

An electrophotographic printing plate precursor free of the above-mentioned organic photoconducting compound soluble in a binder resin has also been known. Such an electrophotographic printing plate precursor comprises a photoconducting layer having an organic photoconducting pigment such as a phthalocyanine pigment dispersed in a binder soluble in an aqueous solution of alkali or alcohol. For example, JP-A-55-105254 and JP-A-55-161250 disclose an electrophotographic printing plate precursor comprising, on an aluminum plate, a photoconducting layer having a phthalocyanine pigment dispersed in a phenolic resin. However, such an electrophotographic printing plate precursor is disadvantageous in that it lacks sensitivity. Thus, an electrophotographic photoreceptor comprising a phthalocyanine pigment dispersed in a binder resin and free of organic photoconducting compound such a hydrazone compound and oxazole compound exhibits an induction effect which causes a drop in sensitivity (see Weigl, *Current Problems in Electrophotography*, p. 278, Water de Gruyter, 1972). It has also been known that the incorporation of an electron-attracting compound such as tetranitrofluorenone and trinitrofluorenone in a photo receptor can reduce the induction effect and hence improve the sensitivity (see *Denshi Shashin Gakkaishi*, vol. 60, 116, 20, 1982). However, due to their toxicity, these electron-attracting compounds can hardly be put into practical use.

As has been described, an electrophotographic printing plate precursor has been desired which exhibits a high sensitivity and no change in electrophotographic properties with time and shows an excellent elutability with an etching solution.

SUMMARY OF THE INVENTION

It is therefore an object of the present invention to provide an electrophotographic photoreceptor which is highly sensitive, particularly to light of a long wavelength from a semiconductor laser or the like, and exhibits a high potential stability, low residual potential and high durability upon repeated use.

It is another object of the present invention to provide an electrophotographic printing plate precursor which can eliminate the above-mentioned conventional disadvantages and exhibits a high sensitivity, excellent age stability, excellent elutability and small printing stain.

These objects of the present invention are accomplished with an electrophotographic photoreceptor for copier or photoprinter comprising a photoconducting layer comprising an electrically conductive support having provided thereon a photoconductive layer comprising a phthalocyanine pigment and at least one of compounds represented by the general formulae (I) and (II), and an electrophotographic printing plate precursor comprising a photoconducting layer containing at least a photoconducting pigment and a binder resin on an electrically conductive layer which is adapted to form a printing plate in a process which comprises forming a toner image by an electrophotographic process, and then removing said photoconducting layer at the non-image portion, characterized in that said photoconducting pigment is a phthalocyanine pigment and said photoconducting layer further contains a compound represented by the general formula (I) or (II):

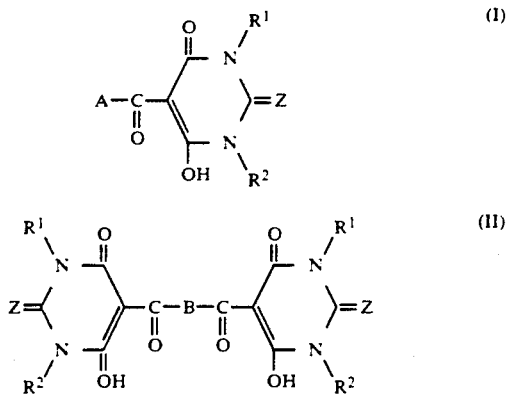

wherein Z represents a sulfur atom or oxygen atom; and $R^1$ and $R^2$ each represents a hydrogen atom or an alkyl, aryl or aralkyl group which may be further substituted by other substituents, $R^1$ and $R^2$ being the same or different.

In the general formula (I), A represents an alkyl group, aryl group, aralky group, or monovalent heterocyclic group which may be further substituted by other substituents. In the general formula (II), B represents an alkylene group, arylene group, polymethylene group or aralkylene group which may be further substituted by other substituents.

A preferred embodiment of the present electrophotographic photoreceptor is an electrophotographic photoreceptor for copier or photoprinter comprising a conductive support, characterized in that said photoconducting layer comprises a phthalocyanine pigment and at least one of the compounds represented by the general formula (I) or (II).

A further preferred embodiment of the present electrophotographic photoreceptor is an electrophotographic photoreceptor for copier or photoprinter comprising a photoconducting layer having a laminated structure comprising a charge-generating layer and a charge-transporting layer on an electrically conductive layer, characterized in that said charge-generating layer comprises a phthalocyanine pigment and at least one of the compounds represented by the general formula (I) or (II).

A still further preferred embodiment of the present electrophotographic photoreceptor is an electrophotographic photoreceptor for copier or photoprinter as defined above, characterized in that the light source of said copier or photoprinter is a laser.

In the present invention, a high sensitivity and high durability electrophotographic photoreceptor which exhibits excellent properties upon repeated use can be obtained.

DETAILED DESCRIPTION OF THE INVENTION

A: Electrophotographic Photoreceptor

Figure 1:
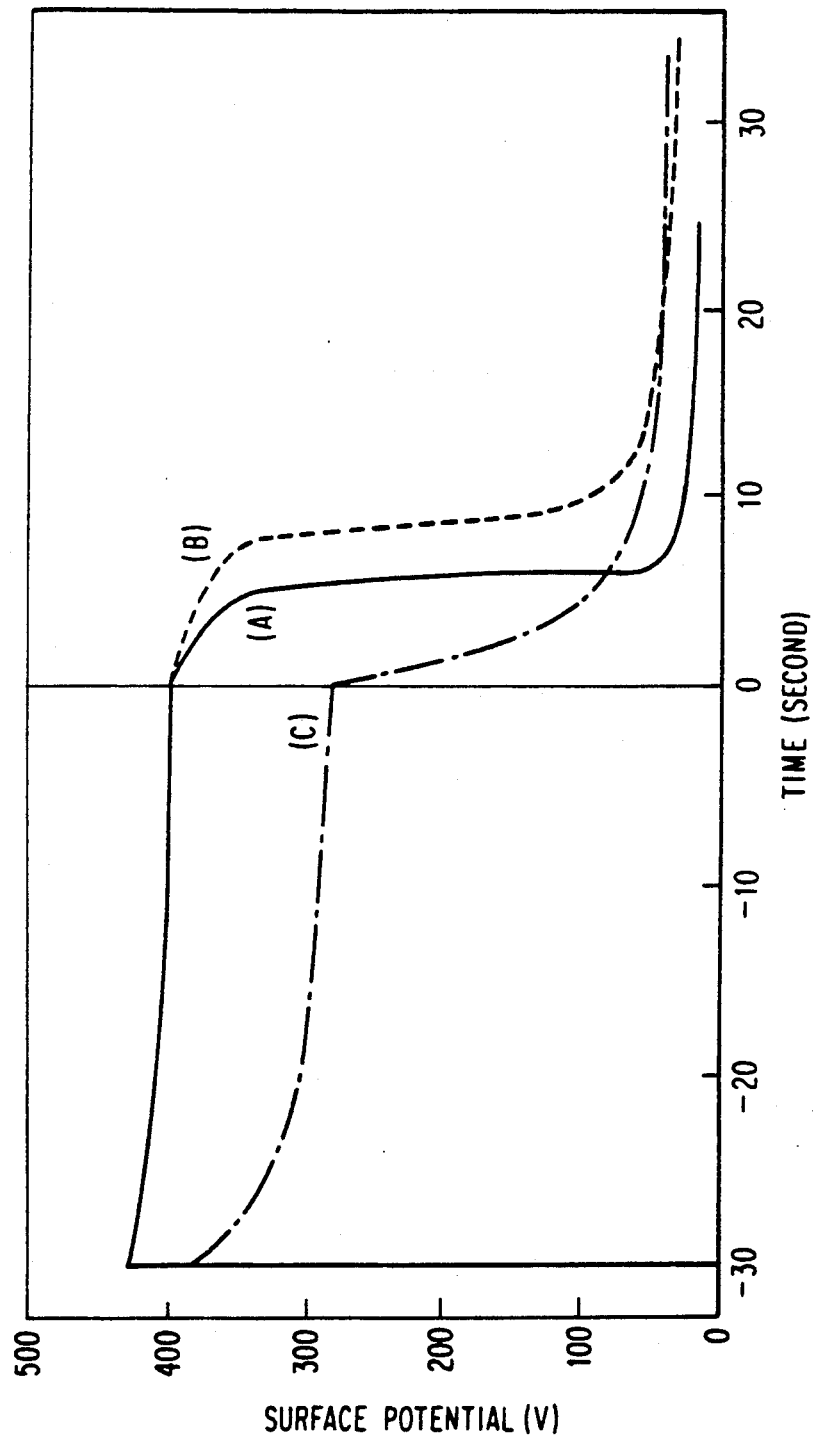
FIG. 1 is a curve illustrating the decay of surface potential on an electrophotographic printing plate precursor wherein the curves A, B and C show the decay of surface potential on the electrophotographic printing plate precursors of Example B-1, Comparative Example B-1 and Comparative Example B-2, respectively.

As the phthalocyanine pigment to be incorporated in the photoconducting layer in the present electrophotographic photoreceptor there can be used any of various phthalocyanine pigments such as those containing different center metals, those having different crystal forms and those containing substituted benzene rings. Examples of such phthalocyanine pigments include metal-free phthalocyanines as described in JP-B-44-14106, JP-B-45-8102, JP-B-46-42511, JP-B-46-42512, and JP-B-49-4338, and JP-A-58-182639.,- and JP-A-62-47054, copper phthalocyanines as described in JP-A-50-38543, JP-A-50-95852, JP-A-51-108847, JP-A-51-109841, titanyl phthalocyanines as described in JP-A-59-49544, JP-A-59-166959, JP-A-62-275272, JP-A-62-286059, JP-A-62-67094, JP-A-63-364, JP-A-63-365, JP-A-63-37163, JP-A-63-57670, JP-A-63-80263, JP-A-63-116158, and JP-A-63-198067, aluminum phthalocyanines as described in JP-A-57-90058, JP-A-62-163060, JP-A-62-133462, JP-A-62-177069, JP-A-63-73529, and JP-A-63-43155, vanadyl phthalocyanines as described in JP-A-57-146255, JP-A-57-147641, and JP-A-57-148747, and halogenated metal phthalocyanines as described in JP-A-59-44053, JP-A-59-128544, JP-A-59-133550, JP-A-59-133551, JP-A-59-174846, JP-A-59-174847, JP-A-60-59354, JP-A-60-260054, JP-A-60-220958, JP-A-62-229254, JP-A-63 17457, JP-A-59-155851, JP-A-63-27562, and JP-A-63-56564. However, the present invention should not be construed as being limited thereto. Various known phthalocyanines can be used.

As typical center metals to be incorporated in these phthalocyanines there have been known copper, nickel, iron, vanadium, aluminum, gallium, indium, silicon, titanium, magnesium, cobalt, platinum, and germanium. In addition, various metal-free phthalocyanines have been known.

The crystal form of these metal or metal-free phthalocyanines can be confirmed by X-ray crystalline diffractometry. For example, copper phthalocyanines have been known to have polymorphisms such as α type, β type, γ type, δ type, ε type, η type and ρ type. Metal-free phthalocyanines have been known to have polymorphisms such as α type, β type, χ type and τ type. Titanyl phthalocyanines have been known to have polymorphisms such as α type, β type and m type. Further, substituted phthalocyanines containing benzene rings substituted by halogen atoms such as fluorine, chlorine and bromine, alkyl group, carboxyl group, amide group, sulfonyl group, or other substituents have been known.

Other examples of phthalocyanine pigments which can be used in the present invention include germanium naphthalocyanines as described in JP-A-63-233886, JP-A-63-186251, and JP-A-63-72761, silicon naphthalocyanines as described in JP-A-63-55556, and JP-A-63-141070, tin naphthalocyanines as described in JP-A-63-186251 and JP-A-64-2061, and various metal naphthalocyanines as described in JP-A-63-72761, and JP-A-63-231355.

These phthalocyanines have different absorption wavelengths and can be properly selected depending on the purpose of application. If applied to a laser beam printer using a semiconductor- laser as light source, a phthalocyanine pigment having absorption in the wavelength range of 780 to 830 nm is preferably used.

The present invention will be further described with reference to the compound of the general formula (I) or (II) which improves the photoconductivity of a photoconducting layer comprising such a phthalocyanine pigment.

In the general formula (I) or (II), $R^1$ and $R^2$ each represents a hydrogen atom or an alkyl, aryl or aralkyl group which may contain substituents. The carbon number of these groups is up to 20, preferably up to 10. If these groups are substituted, examples of such substituents include cyano group, hydroxy group, carboxyl group, nitro group, halogen atom (e.g., chlorine, fluorine, bromine), amino group, alkyl group, alkoxy group, aryl group, aryloxy group, alkoxycarbonyl group, acyloxy group, amino group substituted by alkyl group, aryl group or aralkyl group, and trifluoromethyl group. The carbon number of these substituents which can be specified by a carbon range is up to 20, preferably up to 10. Specific examples of $R^1$ and $R^2$ include straight-chain, branched and substituted alkyl groups such as methyl group, ethyl group, n-propyl group, iso-propyl group, n-butyl group, sec-butyl group, n-hexyl group, 2-ethylhexyl group, fluoromethyl group, chloromethyl group, trifluoromethyl group, perfluoroalkyl group, methoxymethyl group and cyanomethyl group, and aryl groups, substituted aryl groups, aralkyl groups and substituted aralkyl groups such as phenyl group, p-trifluoromethylphenyl group, o-trifluoromethylphenyl group, p-cyanophenyl group, o-cyanophenyl group, p-nitrophenyl group, o-nitrophenyl group, p-bromophenyl group, o-bromophenyl group, p-chlorophenyl group, o-chlorophenyl group, p-fluorophenyl group, o-fluorophenyl group, p-carboxylphenyl group, p-methoxyphenyl group, o-methoxyphenyl group, N,N-diethylaminophenyl group, N,N-diphenylaminophenyl group, N,N-dibenzylaminophenyl group, N,N-dimethylaminophenyl group, naphthyl group, methoxynaphthyl group, N,N-diethylaminonaphthyl group, benzyl group, p-bromobenzyl group, p-cyanobenzyl group, p-nitrobenzyl group, p-trifluoromethylbenzyl group, o-bromobenzyl group, o-cyanobenzyl group, o-nitrobenzyl group, phenylethyl group, 3-phenylpropyl group, p-chlorobenzyl group, and naphthylmethyl group. $R^1$ and $R^2$ may be the same or different.

In the general formula (I), A represents a substituted or unsubstituted alkyl group, substituted or unsubstituted aryl group, a substituted or unsubstituted aralkyl group, or monovalent heterocyclic group which may contain substituents. The carbon number of these alkyl, aryl, and aralkyl groups is up to 20, preferably up to 10.

If these alkyl, aryl, aralkyl or heterocyclic groups are substituted, examples of such substituents include those described with reference to $R^1$ and $R^2$.

Specific examples of the substituted or unsubstituted alkyl, aryl or aralkyl group represented by A include straight-chain, branched and substituted alkyl group such as methyl group, ethyl group, n-propyl group, iso-propyl group, n-butyl group, sec-butyl group, n-hexyl group, 2-ethylhexyl group, fluoromethyl group, chloromethyl group, trifluoromethyl group, perfluoroalkyl group, methoxymethyl group and cyanomethyl group, and unsubstituted and substituted aryl group and unsubstituted and substituted aralkyl group such as phenyl group, p-trifluoromethylphenyl group, o-trifluoromethylphenyl group, p-cyanophenyl group, o-cyanophenyl group, p-nitrophenyl group, o-nitrophenyl group, p-bromophenyl group, o-bromophenyl group, p-chlorophenyl group, o-chlorophenyl group, p-fluorophenyl group, o-fluorophenyl group, p-carboxyphenyl group, p-methoxyphenyl group, o-methoxyphenyl group, N,N-diethylaminophenyl group, N,N-diphenylaminophenyl group, N,N-dibenzylaminophenyl group, N,N-dimethylaminophenyl group; naphthyl group, methoxynaphthyl group, cyanonaphthyl group, nitronaphthyl group, chloronaphthyl group, bromonaphthyl group, fluoronaphthyl group, trifluoromethylnaphthyl group, N,N-diethylaminonaphthyl group, benzyl group, phenylethyl group, 3-phenylpropyl group, p-chlorobenzyl group, p-bromobenzyl group, p-cyanobenzyl group, p-nitrobenzyl group, p-trifluoromethylbenzyl group, o-bromobenzyl group, o-cyanobenzyl group, o-nitrobenzyl group, and naphthylmethyl group.

Examples of monovalent heterocyclic group which may contain substituents represented by A include furan, pyrrole, thiophene, indole, benzofuran, benzothiofuran, oxazole, imidazole, thiazole, isoxazole, pyridine, quinoline, isoquinoline, pyridazine, pyrimidine, pyrazine, phthalazine, and derivatives thereof, such as 2-thio-4-thiazolidinone, 3-pyrazolidinone, 5-isoxazolone, 2-oxazolidone, 2,4-thiazolidinedione, 2-thiophenone, 2-furanone, and 4-pyrimidone.

In the general formula (II), B represents an alkylene, arylene, polymethylene or aralkylene group which may contain substituents.

As arylene group represented by B there can be used a $C_{6-22}$ arylene group. Specific examples of such an arylene group include p-phenylene group, m-phenylene group, o-phenylene group, 1,4-naphthylene group, 2,3-biphenylene group, and 4,4'-biphenylene group. Examples of polymethylene group represented by B include $C_{1-22}$ polymethylene group. Examples of alkylene group represented by B include $C_{1-22}$ alkylene group. Examples of such an alkylene group include methylene group, ethylene group, propylene group, butylene group, pentylidene group, 1,2-dimethylethylene group, 1,3-dimethyltrimethylene group, 1,4-dimethyltetramethylene group, 1,5-dimethylpentamethylene group, 1,6-dimethylhexamethylene group, 1-ethylethylene group, and 1,2-diethylethylene group. As aralkylene group represented by B there can be used a $C_{7-22}$ aralkylene group. Examples of such an aralkylene group include:

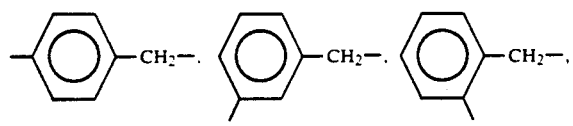

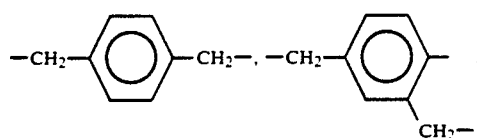

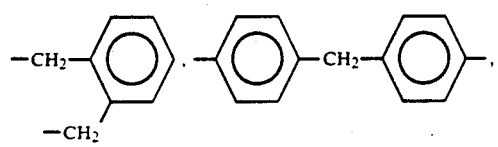

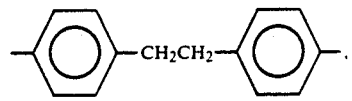

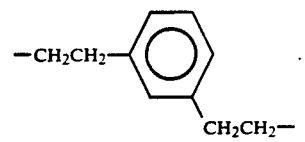

These aralkylene groups may be substituted by substituents. Examples of such substitutes include those described with reference to $R^1$ and $R^2$.

Specific examples of the compounds represented by (I) and (II) will be set forth hereinafter, but the present invention should not be construed as being limited thereto.

Exemplary Compound 1

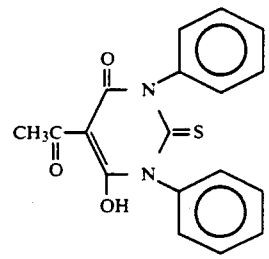

Exemplary Compound 2

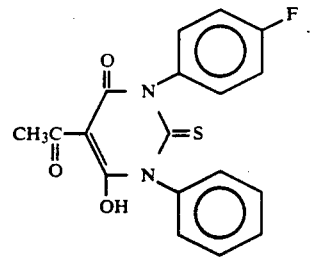

Exemplary Compound 3

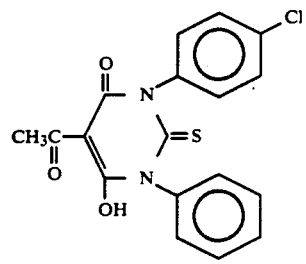

Exemplary Compound 4

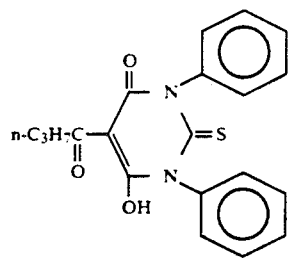
Exemplary Compound 5
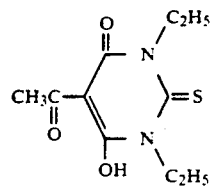
Exemplary Compound 6
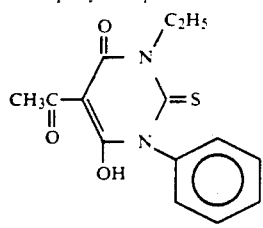
Exemplary Compound 7
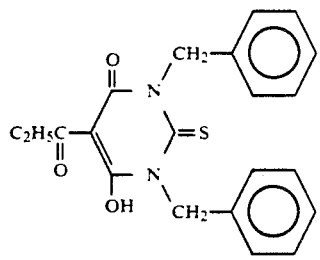
Exemplary Compound 8
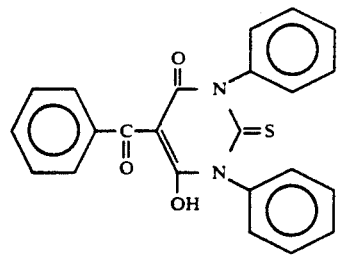
Exemplary Compound 9
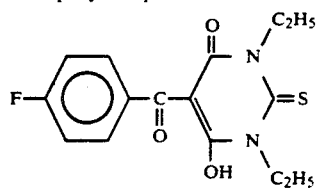
Exemplary Compound 10
-continued

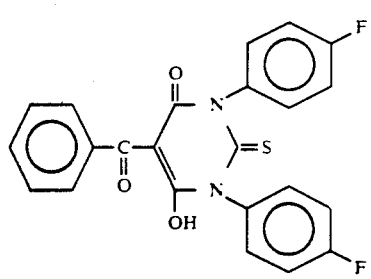
Exemplary Compound 11
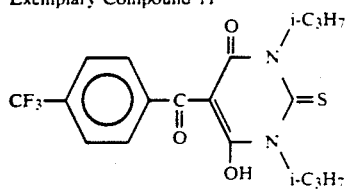
Exemplary Compound 12
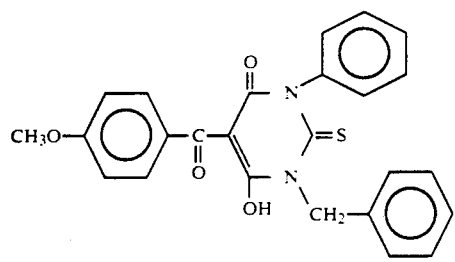
Exemplary Compound 13
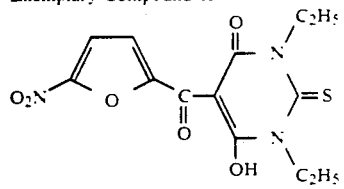
Exemplary Compound 14
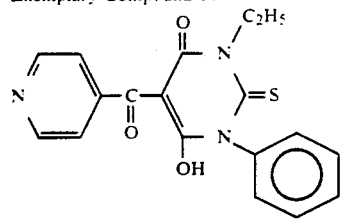
Exemplary Compound 15
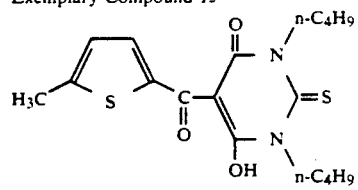
Exemplary Compound 16
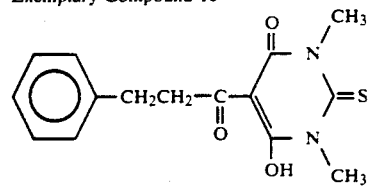

-continued
Exemplary Compound 17
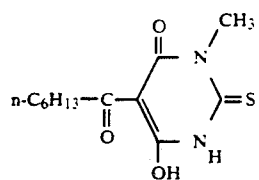
Exemplary Compound 18
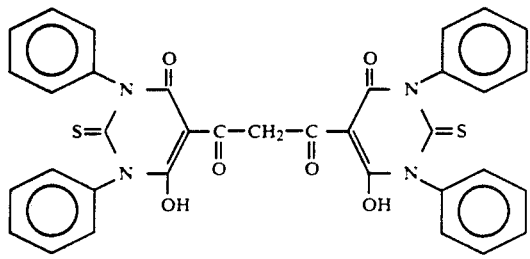
Exemplary Compound 19
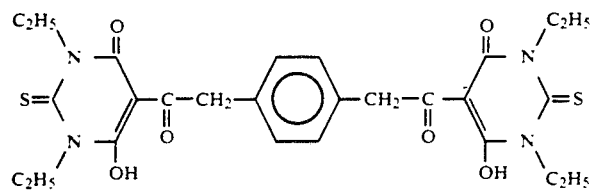
Exemplary Compound 20
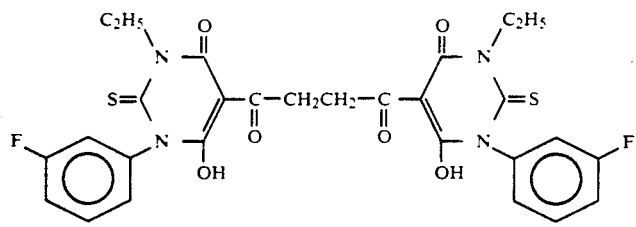
Exemplary Compound 21
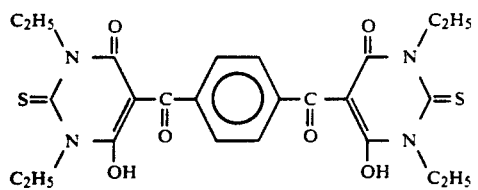
Exemplary Compound 22
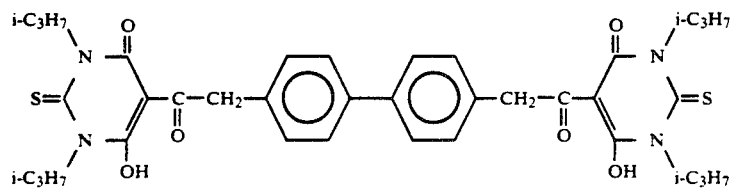
Exemplary Compound 23

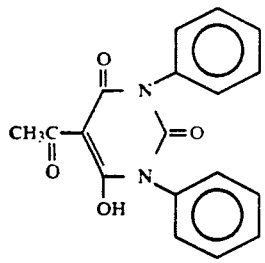

Exemplary Compound 24

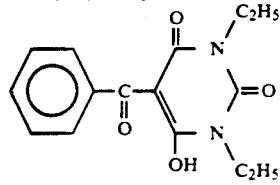

Exemplary Compound 25

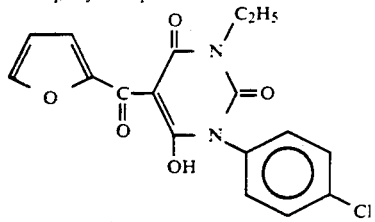

Exemplary Compound 26

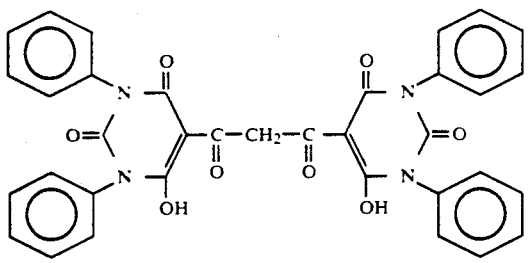

Exemplary Compound 27

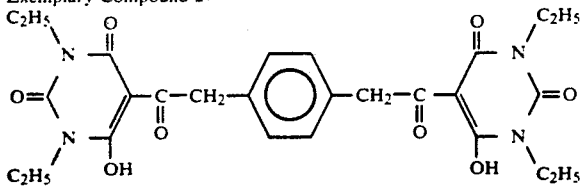

The synthesis of these compounds can be easily accomplished by allowing thiobarbituric acid or barbituric acid and a corresponding organic acid halide or acid anhydride to undergo reaction in the presence of an alkali such as pyridine and triethylamine or a method as described in J. Am. Chem. Soc., Vol. 76, 6185 (1956).

It is unknown how the compound of the present invention works. The compound of the present invention is considered to be a sensitizer for improving the efficiency of production of carriers and improving the sensitivity of light-sensitive materials.

If various additives such as electron-attracting compound, e.g., tetranitrofluorenone and tetracyanoethylene are incorporated with phthalocyanine for the purpose of increasing the sensitivity of phthalocyanine, it normally causes a drop in chargeability and drop in charged potential and a rise in residual potential upon repeated use.

However, the present compound of the general formula (I) or (II) causes no deterioration upon repeated use and sensitizes phthalocyanine and thus is suited for use in a photoreceptor for copiers and photoprinters requiring high sensitivity and excellent repeatability.

The electrophotographic photoreceptor of the present invention comprises a photoconducting layer containing the above-mentioned phthalocyanine pigment and the above-mentioned compound represented by the general formula (I) or (II). Various forms of electrophotographic photoreceptors have been known. The electrophotographic photoreceptor of the present invention may be of any of these types. In general, the electrophotographic photoreceptor of the present invention is used in the following exemplified layer structures:

(1) Layer structure comprising a single photoconducting layer containing a phthalocyanine pigment and the above-mentioned compound of the general formula (I) or (II) on an electrically conductive support;

(2) Layer structure comprising a charge-generating layer containing a phthalocyanine pigment and a compound of the general formula (I) or (II) on an electrically conductive support and a charge-transporting medium layer thereon; and (3) Layer structure comprising a charge-transporting medium layer on an electrically conductive support and a charge-generating layer containing a phthalocyanine pigment and a compound of the general formula (I) or (II).

The preparation of the electrophotographic photoreceptor of the type (1) can be accomplished by dispersing a phthalocyanine pigment in a solution of a compound of the general formula (I) or (II) and a binder, coating the dispersion on an electrically conductive support, and then drying the material, or by dispersing a phthalocyanine pigment in a binder solution, dissolving a compound of the general formula (I) or (II) in the solution, coating the solution on an electrically conductive support, and then drying the material. The electrophotographic photoreceptor of type (1) may comprise a charge-transporting agent as described later in the photoconducting layer for the purpose of facilitating the migration of charge. The electrophotographic photoreceptor of the present invention normally has such a construction. In this layer structure, the thickness of the photoconducting layer is in the range of 3 to 50 $\mu$m, preferably 5 to 30 $\mu$m.

The preparation of the electrophotographic photoreceptor of the type (2) can be accomplished by dispersing a phthalocyanine pigment and a compound of the general formula (I) or (II) in a proper solvent or a solvent optionally with a binder contained therein, or dispersing phthalocyanine pigment in a solvent or a solvent with a binder contained therein, dissolving a compound of the general formula (I) or (II) in the dispersion, coating the solution on an electrically conductive support, drying the material to form a charge-generating layer, coating a solution containing a charge-transporting compound and a binder thereon, and then drying the material to form a charge-transporting layer. In this layer structure, the thickness of the charge-generating layer is in the range of 4 $\mu$m or less, particularly 0.1 to 2 $\mu$m. The thickness of the charge-transporting layer is in the range of 3 to 50 $\mu$m, particularly 5 to 30 $\mu$m.

Alternatively, the charge-generating layer of the present invention can be prepared by providing a thin layer containing a compound of the general formula (I) or (II) on an electrically conductive support, vacuum-depositing a phthalocyanine pigment on the thin layer to form a charge-generating layer so that the diffusion of the solvent for the upper layer causes the phthalocyanine pigment and the compound of the general formula (I) or (II) to be contained therein, or by vacuum-depositing a phthalocyanine pigment on an electrically conductive; support, and then coating a solution containing a compound of the general formula (I) or (II) thereon so that the compound of the general formula (I) or (II) is allowed to be present with the phthalocyanine pigment. In this layer structure, the thickness of the phthalocyanine pigment layer thus vacuum-deposited is preferably in the range of 0.001 to 1 $\mu$m, particularly 0.01 to 0.5 $\mu$m.

The preparation of the electrophotographic photoreceptor of the type (3) can be accomplished by reversing the order of lamination of the charge-generating layer and the charge-transporting layer in the electrophotographic photoreceptor of the type (2).

Since the phthalocyanine pigment itself is capable of transferring charge unlike azo pigment, the present electrophotographic photoreceptor of the type (1) has a relatively excellent repeatability. However, as compared to the electrophotographic photoreceptors of the types (2) and (3), the electrophotographic photoreceptor of the type (1) exhibits a low sensitivity and a drop in charged potential and a slight rise in residual potential upon repeated use.

Therefore, the electrophotographic photoreceptor of the present invention is preferably used in the form of types (2) and (3). In this form, an electrophotographic photoreceptor can be obtained which exhibits an extremely high sensitivity, a high printing resistance and a high durability and exhibits a small change in charged potential and a low residual potential upon repeated use.

The phthalocyanine pigment to be incorporated in the electrophotographic photoreceptor of the type (1), (2) or (3) is ground and dispersed in a known dispersing machine such as ball mill, sand mill, and oscillating mill to a grain diameter of 5 $\mu$m or less, preferably 0.1 to 2 $\mu$m.

If the content of the phthalocyanine pigment in the electrophotographic photoreceptor of the type (1) is too large, it causes a deterioration in sensitivity. If the content of the phthalocyanine pigment is too small, it causes a deterioration in chargeability and a deterioration in the strength of the electrophotographic light-sensitive layer. The content of the phthalocyanine pigment in the electrophotographic light-sensitive layer is in the range of 0.01 to 2 times by weight, preferably 0.05 to 1 time by weight that of the binder.

If a charge-transporting compound is used, its content is in the range of 0.1 to 2 times by weight, preferably 0.3 to 1.3 times by weight that of the binder.

The content of the compound of the general formula (I) or (II) is in the range of 0.01 to 1 time by weight, preferably 0.02 to 0.4 times by weight that of the phthalocyanine pigment.

If the electrophotographic photoreceptors of the types (2) and (3) comprise a disazo compound-containing layer as charge-generating layer, the content of the phthalocyanine pigment is preferably in the range of 0.1 to 50 times by weight that of the binder resin. If the value falls below this range, a sufficient light sensitivity cannot be obtained. The proportion of the charge-transporting compound in the charge-transporting medium is in the range of 0.01 to 10 times by weight, preferably 0.2 to 2 times by weight that of the binder.

In this case, too, the content of the compound of the general formula (I) or (II) is in the range of 0.01 to 1 time by weight, preferably 0.02 to 0.4 times by weight that of the phthalocyanine pigment.

The electrophotographic photoreceptor of the types (2) and (3) can also comprise a charge-transporting compound such as hydrazone compound and oxime compound in the charge-generating layer as described in JP-A-60-196767, JP-A-60-254045, and JP-A-60-262159.

As the charge-transporting material to be incorporated in the light-sensitive layer in the electrophotographic photoreceptor of the type (1) there can be used any of a wide range of known charge-transporting materials. These charge-transporting materials can be classified into two types: electron-transporting compounds and positive hole-transporting compounds.

Examples of such an electron-transporting compound include compounds containing an electrophilic group, such as 2,4,7-trinitro-9-fluorenone, 2,4,5,7-tetranitro-9-fluorenone, 9-dicyanomethylene-2,4,7-trinitrofluorenone, 9-dicyanomethylene-2,4,5,7-tetranitrofluorenone, tetranitrocarbazolechloranil, 2,3-dichloro-5,6-dicyanobenzoquinone, 2,4,7-trinitro-9,10-phenanthrequinone, tetrachlorophthalic anhydride, tetracyanoethylene, and tetracyanoquinonedimethane.

Examples of compounds transporting positive holes include compounds containing electron-donating group. Examples of high molecular compounds containing electron-donating group include:

(1) Polyvinyl carbazole and its derivatives as disclosed in JP-B-34-10966;

Vinyl polymers such as polyvinyl pyrene, polyvinyl anthracene, poly-2-vinyl-(4'-dimethylaminophenyl)- 5-phenyloxazole and poly-3-vinyl-N-ethylcarbazole, as disclosed in JP-B-43-18674 and JP-B-43-19192;

(3) Polymers such as polyacenaphthylene, polyindene and acenaphthylene-styrene copolymer, as disclosed in JP-B-43-19193;

(4) Condensed resin such as pyrene-formaldehyde resin, bromopyrene-formaldehyde resin and ethylcarbazole-formaldehyde resin, as disclosed in JP-B-56-13940; and (5) Various triphenylmethane polymers as disclosed in JP-A-56-90883 and JP-A-56-161550.

Examples of low molecular compounds containing an electron-donating group include:

(6) Triazole derivatives as disclosed in U.S. Pat. No. 3,112,197;

(7) Oxadiazole derivatives as disclosed in U.S. Pat. No. 3,189,447;

(8) Imidazole derivatives as disclosed in JP-B-37-16096;

(9) Polyarylalkane derivatives as disclosed in U.S. Pat. Nos. 3,615,402, 3,820,989, and 3,542,544, JP-B-45-555, and JP-B-51-10983, and JP-A-51-93224, JP-A-55-108667, JP-A-55-156953, and JP-A-56-36656;

(10) Pyrazolidone derivatives and pyrazolone derivatives as disclosed in U.S. Pat. Nos. 3,180,729, and 4,278,746, and JP-A-55-88064, JP-A-55-88065, JP-A-49-105537, JP-A-55-51086, JP-A-56-80051, JP-A-56-88141, JP-A-57-45545, JP-A-54-112637, and JP-A-55-74546;

(11) Phenylenediamine derivatives as disclosed in U.S. Pat. No. 3,615,404, JP-B-51-10105, JP-B-46-3712, and JP-B-47-28336, and JP-A-54-83435, JP-A-54-110836, and JP-A-54-119925;

(12) Arylamine derivatives as disclosed in U.S. Pat. Nos. 3,567,450, 3,180,703, 180,703, 3,240,597, 3,658,520, 4,232,103, 4,175,961, and 4,012,376, West German Patent (DAS) 1110518, JP-A-55-144250, JP-A-56-119132, and JP-A-56-22437, and JP-B-39-27577;

(13) Amino-substituted chalcone derivatives as disclosed in U.S. Pat. No. 3,526,501;

(14) N,N-bicarbazyl derivatives as disclosed in U.S. Pat. No. 3,542,546;

(15) Oxazol derivatives as disclosed in U.S. Pat. No. 3,257,203:

(16) Styrylanthracene derivatives s disclosed in JP-A-56-46234;

(17) Fluorenone derivatives as disclosed in JP-A-54-110837;

(18) Hydrazone derivatives as disclosed in U.S. Pat. No. 3,717,462, and JP-A-54-59143 (corresponding to U.S. Pat. 4,150,987) , JP-A-55-52063, JP-A-55-52064, JP-A-55-46760, JP-A-55-85495, JP-A-57-11350, JP-A-57-148749, and JP-A-57-104144;

(19) Benzidine derivatives as disclosed in U.S. Pat. Nos. 4,047,948, 4,047,949, 4,265,990, 4,273,846, 4,299,897, and 4,306,008; and

(20) Stilbene derivatives as disclosed in JP-A-58-190953, JP-A-59-95540, JP-A-59-97148, and JP-A-59-195658.

The photoconducting materials to be used in the present invention are not limited to the above-mentioned compounds (1) to (20) . Any known photoconducting material can be used in the present invention.

These photoconducting materials can be optionally used in combination.

Examples of electrically conductive support to be incorporated in the present electrophotographic photoreceptor include plate and drum of metal such as aluminum, copper, zinc and stainless steel, support material obtained by vacuum-depositing or dispersion-coating an electrically conductive material such as aluminum, indium oxide, $SnO_2$ and carbon on a sheet or cylindrical substrate of plastic, paper or the like, support material comprising an electrically conductive polymer provided on such a substrate, and paper and paper tube treated with an electrically conductive material such as inorganic salt, e.g., sodium chloride, calcium chloride, and organic quaternary ammonium salt, and carbon-incorporated molded phenolic resin drum and Bakelite drum.

As resin to be incorporated in the charge-generating layer in the electrophotographic photoreceptors of the types (2) and (3) there can be selected from a wide range of insulating resins. Examples of such a resin include polyester resin, cellulose resin, acrylic resin, polyamide resin, polyvinyl butyral resin, phenoxy resin, polyvinyl formal resin, polycarbonate resin, styrene resin, polybutadiene resin, polyurethane resin, epoxy resin, silicone resin, vinyl chloride resin, and vinyl chloride-vinyl acetate resin. The present invention is not limited to these resins.

As resin to be incorporated in the charge-transporting layer there is preferably used a high dielectric constant hydrophobic insulating film-forming high molecular polymer.

Specific examples of such a high molecular polymer include polycarbonate, polyester, methacrylic resin, acrylic resin, polyvinyl chloride, polyvinylidene chloride, polystyrene, polyvinyl acetate, styrenebutadiene copolymer, vinylidene chloride-acrylonitrile copolymer, vinyl chloride-vinyl acetate copolymer, vinyl chloride-vinyl acetate-maleic anhydride copolymer, silicone resin, silicone-alkyd resin, phenolformaldehyde resin, styrene-alkyd resin, and poly-N-vinyl carbazole. However, the present invention should not be construed as being limited to these polymers.

As binder to be incorporated in the photoconducting layer in the electrophotographic photoreceptor of the type (1) there can be properly selected from those to be incorporated in the above-mentioned charge-generating layer and charge-transporting layer.

These binders can be used singly or in admixture.

In the preparation of the present electrophotographic photoreceptor, there can be used additives such as a plasticizer and sensitizer in combination with such a binder.

Examples of such a plasticizer include biphenyl, biphenyl chloride, o-terphenyl, p-terphenyl, dibutyl phthalate, dimethyl glycol phthalate, dioctyl phthalate, triphenyl phosphate, methyl naphthaline, benzophenone, chlorinated paraffin, polypropylene, polystyrene, dilauryl thiodipropinoate, 3,5-dinitrosalicylic acid, dimethyl .phthalate, dibutyl phthalate, diisobutyl adipate, dimethyl sebacate, dibutyl sebacate, butyl laurate, methyl phthalyl ethyl glycolate, and various fluorohydrocarbons.

In addition, a silicone oil or the like can be incorporated in the electrophotographic photoreceptor to improve the surface properties thereof.

Examples of sensitizers to be used in the present invention include chloranil, tetracyanoethylene, methyl violet, Rhodamine B, cyanine dye, melocyanine dye, pyrilium dye, thiapyrilium dye, and compounds as described in JP-A-58-65439, JP-A-58-102239, JP-A-58-129439, and JP-A-62-71965.

As solvent for the coating solution there can be used alcohol (e.g., methanol, ethanol, isopropanol), ketone (e.g., acetone, methyl ethyl ketone, methylisobutyl ketone, cyclohexanone), amide (e.g., N,N-dimethylformamide, N,N-dimethylacetamide), ester (e.g., methylacetate, ethyl acetate, butyl acetate), ether (e.g., tetrahydrofuran, dioxane, monoglyme, diglyme), or halogenated hydrocarbon (e.g., methylene chloride, chloroform, methyl chloroform, carbon tetrachloride, monochlorobenzene, dichlorobenzene), singly or in admixture.

The coating can be accomplished by commonly used coating method such as spray coating, roller coating, spinner coating, blade coating, and dip coating.

In the present invention, an adhesive layer or barrier layer can be optionally provided between the electrically conductive support and the photoconducting layer. As materials for such an adhesive layer or barrier layer there can be used the above-mentioned high molecular compounds used as binder. In addition, there can be used gelatin, casein, polyvinyl alcohol, ethyl cellulose, carboxymethyl cellulose, vinylidene chloride polymer latex as described in JP-A-59-84247, styrene-butadiene polymer latex as described in JP-A-59-114544, or aluminum oxide. The thickness of such a layer is preferably in the range of 0.1 to 5 μm.

In the present invention, an overcoat layer can be optionally provided on the photoconducting layer. Such an overcoat layer may be a mechanically matted layer or a resin layer containing a matting agent. Examples of such a matting agent include silicon dioxide, glass grain, alumina, starch, titanium oxide, zinc oxide, grain of polymer such as polymethyl methacrylate, polystyrene and phenolic resin, and matting agents as described in U.S. Pat. Nos. 2,701,245, and 2,992,102. These matting agents can be used in combination..

As the resin to be incorporated in the overcoat layer there can be used resin incorporated in the photoconducting layer. In addition, there can be used any resin selected from various known resins.

As has been described, the electrophotographic photoreceptor of the present invention is an electrophotographic photoreceptor which exhibits an excellent sensitivity, a high printing resistance and a high durability and exhibits a small change in charged potential and a low residual potential upon repeated use.

The electrophotographic photoreceptor of the present invention can be widely applied to printers using laser or CRT as light source, not to mention electrophotographic copiers. In particular, since the electrophotographic photoreceptor of the present invention has a high sensitivity up to long wavelength range, it can be suitably applied to laser printers using semiconductor laser, He-Ne laser or the like as light source.

B: Electrophotographic Printing Plate Precursor

The first component constituting the photoconducting layer in the electrophotographic printing plate precursor of the present invention is a phthalocyanine pigment as photoconducting pigment. As such a phthalocyanine pigment there can be used one similar to those disclosed with reference to the electrophotographic photoreceptor.

Electrophotographic printing plate precursors are often required to have a higher charge retention than electrophotographic photoreceptors for copiers and photoreceptors for photoprinters. Therefore, a phthalocyanine pigment which exhibits a high charge retention (capability of retaining surface potential in a dark place) is preferably used.

The content of the phthalocyanine pigment in the photoconducting layer is in the range of 3 to 50% by weight, preferably 5 to 30% by weight based on the solid content in the photoconducting layer.

The second component constituting the electrophotographic printing plate precursor of the present invention is a binder resin. Any binder resin can be used so far as it does not elute toner image portions and 's dissolved in or swells with a solvent which elutes non-image portions (i.e., photoconducting layer). Preferably, a resin which is dissolved in or swells with an alcohol and/or alkaline aqueous solution is used. Examples of such a resin include phenolic resin, styrene/maleic anhydride copolymer, vinyl acetate, crotonic acid copolymer, vinyl acetate/maleic anhydride copolymer, alcohol-soluble nylon, and dimers or higher copolymers of acid group-containing monomers such as acrylic acid, methacrylic acid, crotonic acid and itaconic acid with monomers such as methacrylic ester, acrylic ester and styrene. Any copolymers containing acid group can be used.

Specific examples of such copolymers containing acid group will be set forth below, but the present invention should not be construed as being limited thereto.

(1) Benzyl methacrylate-methacrylic acid copolymer (molar proportion: 60:40)
(2) Benzyl methacrylate-methacrylic acid-hydroxymethyl methacrylate copolymer (molar proportion: 60:20:20)
(3) Methyl methacrylate-methacrylic acid-hydroxymethyl methacrylate copolymer (molar proportion: 70:10:20)
(4) Methyl methacrylate-ethyl methacrylate-acrylic acid copolymer (molar proportion: 50:20:30)
(5) Benzyl methacrylate-methyl methacrylate-acrylic acid copolymer (molar proportion: 50:20:30)
(6) Methyl methacrylate-hydroxyethyl methacrylate-acrylonitrile-acrylic acid copolymer (molar proportion: 40:20:30:10)

(7) Benzyl methacrylate-hydroxyethyl methacrylate-acrylonitrile-methacrylic acid copolymer (molar proportion: 20:20:50:10)
(8) Vinyl acetate-crotonic acid copolymer (molar proportion: 90:10)
(9) Vinyl acetate-vinyl hexanate-crotonic acid copolymer (molar proportion: 85:5:10)
(10) Vinyl acetate-maleic anhydride copolymer (molar proportion: 80:20)
(11) Styrene-maleic anhydride copolymer (molar proportion: 50:50)
(12) Styrene-hydroxyethyl methacrylate-methacrylic acid copolymer (molar proportion: 50:20:30)
(13) Styrene-methacrylic acid-methyl methacrylate copolymer (molar proportion: 40:30:30)

These resins can be used singly or in admixture.

The third component constituting the electrophotographic printing plate precursor of the present invention is a compound represented by the general formula (I) or (II) as described with reference to the electrophotographic photoreceptor.

The third component serves as a sensitizer for improving the photoconductivity of the photoconducting layer made of the above-mentioned phthalocyanine pigment and binder resin. As mentioned above, if the photoconducting layer is free of the third component, it gives an induction effect which causes a delay in the decay of surface potential shortly after irradiation with light, resulting in a drop in sensitivity. The mechanism of this phenomenon is not yet made clear. It is thought that carriers produced by the irradiation with light are caught by carrier traps present on the surface of phthalocyanine grains, and during this period the surface potential shows no decay. The compound of the present invention is considered to be a sensitizer which serves to minimize the induction effect and hence reduce the period during which the surface potential shows no decay (induction period), improving the sensitivity.

The content of the compound of the general formula (I) or (II) as the third component is not specifically limited but is preferably in the range of 1 to 100% by weight, more preferably 2 to 40% by weight based on the weight of phthalocyanine pigment.

The photoconducting layer in the electrophotographic printing plate precursor of the present invention can comprise various known additives which have heretofore been used for electrophotographic photoreceptors besides the compound of the present invention. Examples of such additives include chemical sensitizers for improving electrophotographic sensitivity, charge-transporting agents, various plasticizers for improving film-forming properties, and surface active agents. Examples of chemical sensitizers include electron-attracting compounds such as p-benzoquinone, chloranil, fluoranil, bromanil, dinitrobenzene, anthraquinone, 2,5-dichlorobenzoquinone, nitrophenol, tetrachlorophthalic anhydride, 2,3 dichloro-5,6-dicyanobenzoquinone, dinitrofluorenone, tri nitrofluorenone a nd tetracyanoethylene, and compounds as described in JP-A58-65439, JP-A-58-102239, JP-A-58-129439, and JP-A-62-71965.

Examples of charge-transporting agents include:
(a) Triazole derivatives as disclosed in U.S. Pat. No. 3,112,197;
(b) Oxadiazole derivatives as disclosed in U.S. Pat. No. 3,189,447;
(c) Imidazole derivatives as disclosed in JP-B-37-16096;
(d) Polyarylalkane derivatives as disclosed in U.S. Pat. Nos. 3,615,402, 3,820,989, and 3,542,544, JP-B-45-555, and JP-B-51-10983, and JP-A-51-93224, JP-A-55-108667, JP-A-55-156953, and JP-A-56-36656;
(e) Pyrazoline derivatives and pyrazolone derivatives as disclosed in U.S. Pat. Nos. 3,180,729, and 4,278,746, and JP-A-55-88064, JP-A-55-88065, JP-A-49-105537, JP-A-55-51086, JP-A-56-80051, JP-A-56-88141, JP-A-57-45545, JP-A-54-112637, and JP-A-55-74546;
(f) Phenylenediamine derivatives as disclosed in U.S. Pat. Nos. 3,615,404, JP-B-51-10105, JP-B-46-3712, and JP-B-47-28336, and JP-A-54-83435, JP-A-54-110836, and JP-A-54-119925;
(g) Arylamine derivatives as disclosed in U.S. Pat. Nos. 3,567,450, 3,180,703, 3,240,597, 3,658,520, 4,232,103, 4,175,961, and 4,012,376, West German Patent (DAS) 1,110,518, JP-B-49-35702, and JP-B-39-27577, and JP-A-55-144250, JP-A-56-119132, and JP-A-56-22437;
(h) Amino-substituted chalcone derivatives as disclosed in U.S. Pat. No. 3,526,501;
(i) N,N-bicarbazyl derivatives as disclosed in U.S. Pat. No. 3,542,546;
(j) Oxazole derivatives as disclosed in U.S. Pat. 3,257,203;
(k) Styrylanthracene derivatives as disclosed in JP-A-56-46234;
(l) Fluorenone derivatives as disclosed in JP-A-54-110837;
(m) Hydrazone derivatives as disclosed in U.S. Pat. No. 3,717,462, and JP-A-54-59143 (corresponding to U.S. Pat. No. 4,150,987), JP-A-55-52063, JP-A-55-52064, JP-A-55-46760, JP-A-55-85495, JP-A-57-11350, JP-A-57-148749, and JP-A-57-104144;
(n) Benzidine derivatives as disclosed in U.S. Pat. Nos. 4,047,948, 4,047,949, 4,265,990, 4,273,846, 4,299,897, and 4,306,008;
(o) Stilbene derivatives as disclosed in JP-A-58-190953, JP-A-59-95540, JP-A-59-97148, JP-A-59-195658, and JP-A-62-36674;
(p) Polyvinyl carbazole and its derivatives as disclosed in JP-B-34-10966;
(q) Vinyl polymers such as polyvinyl pyrene, polyvinyl anthracene, poly-2-vinyl-4-(4'-dimethylaminophenyl)-5-phenyloxazole and poly-3-vinyl-N-ethylcarbazole, as disclosed in JP-A-43-18674, and JP-A-43-19192;
(r) Polymers such as polyacenaphthylene, polyindene and copolymer of acenaphtylene and styrene, as disclosed in JP-B-43-19193;
(s) Pyrene-formaldehyde resin, bromopyrene-formaldehyde resin and ethyl carbazole-formaldehyde resin as disclosed in JP-B-56-13940; and
(t) Various triphenyl methane polymers as disclosed in JP-A-56-90883, and JP-A-56-161550.

The charge-transporting agent to be used in the present invention is not limited to the compounds (a) to (t). Any known charge-transporting agents can be used in the present invention. These organic photoconducting compounds can be optionally used in combination.

Examples of plasticizers which can be incorporated in the photoconducting layer to improve the flexibility thereof include dimethyl phthalate, dibutyl phthalate, dioctyl phthalate, triphenyl phosphate, diisobutyl adipate, dimethyl sebacate, dibutyl sebacate, butyl laurate, methyl phthalyl ethyl glycolate, and dimethyl glycol phthalate. These plasticizers can be incorporated in the photoconducting layer in such a manner that the static characteristics and etchicability thereof cannot be deteriorated.

If the thickness of the photoconducting layer in the present invention is too small, the photoconducting layer cannot be charged with a surface potential required for development. On the contrary, if the thickness of the photoconducting layer is too large, a planar etching called side etching takes place during the removal of the photoconducting layer, making it impossible to obtain an excellent printing plate. Therefore, the thickness of the photoconducting layer is in the range of 0.1 to 30 μm, preferably 0.5 to 10 μm.

Examples of electrically conductive support which can be used in the present invention include electrically conductive material having a hydrophilic surface such as plastic sheet comprising an electrically conductive surface, or solvent-impermeable and electrically conductive paper, aluminum plate, zinc plate, bimetal plate, e.g., copper-aluminum plate, copper-stainless steel plate and chromium-copper plate, and trimetal plate, e.g., chromium-copper-aluminum plate, chromium-lead-iron plate and chromium-copper-stainless plate. The thickness of such an electrically conductive support is preferably in the range of 0.1 to 3 mm, particularly 0.1 to 0.5 mm. Particularly preferred among these support materials is aluminum plate. The aluminum plate to be used in the present invention is a plate of pure aluminum containing aluminum as the main component or an aluminum alloy containing a slight amount of hetero atoms. However, the composition of the aluminum plate to be used in the present invention is not specifically limited. Any known commonly used aluminum material can be used.

The aluminum plate can be grained or anodized in a known process before use. Prior to graining, the aluminum plate is optionally degreased with a surface active agent or alkaline aqueous solution to remove a rolling oil from the surface thereof. Examples of graining processes include a process which comprises mechanically roughening the surface of the material, a process which comprises electrochemically solving the surface of the material, and a process which comprises chemically and selectively solving the surface of the material. The mechanical roughening can be accomplished by any known process such as ball abrasion, brush abrasion, blast abrasion and buffing. The electrochemical roughening can be accomplished by passing direct or alternating current through the material in a hydrochloric acid or nitric acid electrolyte. Alternatively, a combination of direct current and alternating current can be passed through the material as disclosed in JP-A-54-63902.

The aluminum plate thus roughened is then optionally etched with an alkali and neutralized.

The aluminum thus treated is then anodized. As the electrolyte to be used in the anodization there can be used sulfuric acid, phosphoric acid, oxalic acid, chromic acid or a mixture thereof. The concentration of the electrolyte is properly determined depending on the kind of the electrolyte. The anodization conditions vary with the kind of the electrolyte and cannot be unequivocally specified. In general, the anodization is preferably effected at an electrolyte concentration of 1 to 80% by weight, a solution temperature of 5° to 70° C., a current density of 5 to 60 A/dm$^2$, and a voltage of 1 to 100 V over 10 seconds to 50 minutes. The quantity of film thus anodized is preferably in the range of 0.1 to 10 g/m$^2$, more preferably 1 to 6 g/m$^2$.

Alternatively, as disclosed in JP-B-47-5125, the aluminum plate which has been anodized maybe preferably dipped in and treated with an aqueous solution of silicate of alkaline metal. As disclosed in U.S. Pat. No. 3,658,662, silicate electrode position can be effectively used. As disclosed in West German Patent Disclosure 1,621,478, treatment with a polyvinylsulfonic acid can be suitably used.

The electrophotographic printing plate precursor of the present invention can optionally comprise an alkali-soluble interlayer made of casein, polyvinyl alcohol, ethyl cellulose, phenolic resin, styrene-maleic anhydride copolymer, polyacrylic acid or the like between the electrically conductive support and the photoconducting layer for the purpose of improving the adhesion therebetween and the static characteristics of the electrophotographic printing plate precursor.

The electrophotographic printing plate precursor of the present invention can also optionally comprise, on the photoconducting layer, an overcoat layer capable of being removed at the same time with the removal of the photoconducting layer for the purpose of improving the static characteristics, developability upon toner development, image characteristics and printability. This overcoat layer may be a mechanically matted layer or a resin layer containing a matting agent. Examples of such a matting agent include silicon dioxide, glass grain, alumina, starch, titanium oxide, zinc oxide, grain of polymer such as polymethyl methacrylate, polystyrene and phenolic resin, and matting agents as disclosed in U.S. Pat. Nos. 2,701,245, and 2,992,101. Two or more of these matting agents can be used in combination. As the resin to be incorporated in the overcoat layer, these can be properly selected depending on the combination with an etching solution for removing the photoconducting layer. Specific examples of such a resin include gum arabic, glue, cellulose, starch, polyvinyl alcohol, polyethylene oxide, polyacrylic acid, polyacrylamide, polyvinyl methyl ether, epoxy resin, phenolic resin, polyamide, and polyvinyl butyral. Two or more of these resins can be used in combination.

In the present invention, any electrophotographic toner such as dry developing agent and liquid developing agent can be used so far as it has resistance to the etching solution for removing the non-image portions and serves to prevent the photoconducting layer on the toner image portion from being eluted with the etching solution. In order to obtain a high resolution image, a liquid developing agent can be preferably used. A toner which can provide a hydrophobic and ink-accepting toner image can also be preferably used. Examples of materials for toner grains include high molecular compounds such as homopolymer and copolymer of polystyrene resin, polyvinyl toluene resin, polyester resin and acrylester, homopolymer and copolymer of methacrylate ester, ethylene copolymer, cyclized rubber, homopolymer and copolymer of vinyl acetate, and vinyl chloride. The toner can comprise coloring agents such as pigment and dye, i.e., carbon black, nigrosine pigment, phthalocyanine blue, phthalocyanine green, benzidine yellow, alkali blue and Carmin 6 B so far as they do not adversely affect the fixing properties, dispersibility and etching resistance of the toner. The toner can further comprise various charge adjustors and other additives.

As the etching solution for removing the photoconducting layer on the toner image portions after the formation of toner images there can be used any solvent capable of removing the photoconducting insulating layer. Therefore, the etching solution to be used in the present invention is not specifically limited. Preferably, an alkaline solvent can be used. The term "alkaline solvent" as used herein means an aqueous solution containing an alkaline compound, organic solvent containing an alkaline compound, or a mixture thereof. Examples of such an alkaline compound include inorganic and organic alkaline compounds such as sodium hydroxide, potassium hydroxide, sodium carbonate, sodium silicate, potassium silicate, sodium metasilicate, potassium metasilicate, sodium phosphate, potassium phosphate, ammonia, and aminoalcohol, e.g., monoethanolamine, diethanolamine and triethanolamine. As the solvent for the etching solution there can be used water or any organic solvent as described above. In view of odor and environmental protection, an etching solution containing water as main component can be preferably used. Such an etching solution can also optionally comprise various organic solvents. Preferred examples of such organic solvents include lower alcohols or aromatic alcohols such as methanol, ethanol, propanol, butanol, benzyl alcohol and phenethyl alcohol, cellosolves such as ethylene glycol, diethylene glycol, triethylene glycol and polyethylene glycol, and aminoalcohols such as monoethanolamine, diethanolamine and triethanolamine. The etching solution can also comprise a surface active agent, an anti-foaming agent, and optionally various additives.

The process for the preparation of a printing plate from the electrophotographic printing plate precursor of the present invention will be described hereinafter. An image is formed on the electrophotographic printing plate precursor of the present invention in the conventional known process. In particular, the electrophotographic printing plate precursor is substantially uniformly charged in a dark place, and then imagewise exposed to light to form a static latent image thereon. Examples of exposure processes include reflective imagewise exposure using a xenon lamp, tungsten lamp, fluorescent lamp or the like as light source, contact exposure through a transparent positive film, and scanning exposure using laser, light-emitting diode or the like. Examples of light sources to be used in the scanning exposure include lasers such as helium-neon laser, helium-cadmium laser, argon ion laser, crypton ion laser, YAG laser, ruby laser, nitrogen laser, dye laser, excimer laser, semiconductor laser (e.g., GaAs/GaAlAs, InGaAsP), Alexandrite laser, copper vapor laser and erbium laser. The scanning exposure can also be effected using a light-emitting diode or liquid crystal shutter (including a line printer type light source using an array of light-emitting diodes or liquid crystal shutters).

Subsequently, the static latent image is developed with a toner. The development can be effected in either a dry process (e.g., cascade development, magnetic brush development, powder cloud development) or a liquid process. In particular, the liquid development process can be suitably used to prepare a printing plate which can form a fine image thereon. Alternatively, positive-positive development can be effected in a positive development process. Furthermore, negative-positive development can be effected in a reverse development process under the application of a suitable bias voltage. The toner image thus formed can be then fixed in any known fixing process such as heat fixing process, pressure fixing process and solvent fixing process. The toner image thus formed can serve as a resist to remove the photoconducting layer from the non-image portions with an etching solution to prepare a printing plate.

In the present invention, a copier means a generally known copy machine to obtain a so-called copy of the original. Generally, a printer is a machine which outputs the degitalized data as a hard copy. Of the printer, a photoprinter means a hard copy machine comprising a function which exposes an electrophotographic photoreceptor by on and off the light transmittance of a light source such as a laser and a LED, and a liquid crystal shutter.

SYNTHESIS EXAMPLE

Synthesis of Exemplary Compound (3)

33.1 g (0.1 mol) of N-(p-chlorophenyl)-N'-phenylthiobarbituric acid and 24.0 g (0.3 mol) of pyridine were dissolved in 1 of chloroform. 12.1 g (0.15 mol) of acetyl chloride was dropwise added to the solution under cooling with water. The mixture was then stirred at room temperature over 2 hours. The solvent was then distilled off under reduced pressure. 500 ml of ethanol was then added to the material. The mixture was then stirred and cooled. As a result, a light yellow solid was deposited. After being filtered off, the light yellow solid was recrystallized from 3 of ethanol to obtain 23 g (yield: 66%) of the desired exemplary compound (3).

Elementary analysis:

|  | Calculated % | | Found % |
| --- | --- | --- | --- |
| H | 3.52 | | 3.49 |
| C | 57.99 | | 57.95 |
| N | 7.51 | | 7.61 |
| Cl | 9.51 | | 9.67 |
| S | 8.60 | | 8.68 |
| H$^1$-NMR: | δ 2.8 | s 3H | |
| | δ 7.1–7.7 | m 9H | |
| | δ 17.3 | s 1H | |
| Mass: | M$^+$ 372 | | |

The present invention will be further described in the following examples hereinafter, but the present invention should not be construed as being limited thereto.

EXAMPLE A-1

3.0 parts by weight of an e type copper phthalocyanine (Liophoton ERPC, available from Toyo Ink Manufacturing Co., Ltd.), 0.3 parts by weight of Exemplary Compound (1), 3.0 parts by weight of a polyester resin (Vylon 200, available from Toyobo Co., Ltd.), 3.0 parts by weight of hydrazone compound of the general formula:

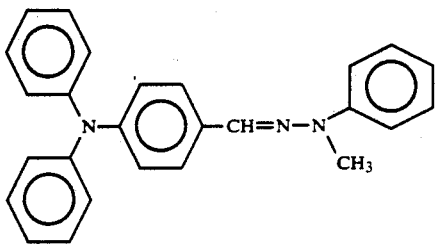

and 100 parts by weight of tetrahydrofuran were charged into a 500-ml glass vessel with glass beads. The material was subjected to dispersion by means of a paint shaker (available from Toyo Seiki Seisakusho K.K.) over 60 minutes. The glass beads were then filtered off to obtain a dispersion for a photoconducting layer.

The dispersion for photoconducting layer was then coated on an electrically conductive support (obtained by vacuum-depositing aluminum on the surface of a 75-μm thick polyethylene terephthalate film; surface resistance: $10^3$ Ω) by means of a wire round rod, and dried to obtain an electrophotographic photoreceptor comprising a 20-μm thick photoconducting layer.

The electrophotographic photoreceptor thus prepared was then measured for electric properties by means of EPA-8100 (available from Kawaguchi Denki K.K.) in a static process. In particular, the specimen was corona-charged at +8.0 kv and then exposed to monochromatic light of a wavelength of 780 nm at an intensity of 1 mW/m². The specimen was evaluated for surface potential $V_O$ developed shortly after charging, charge retention $DD_{10}$ represented by the ratio of the surface potential developed 10 seconds after charging to $V_O$, sensitivity represented by exposure $E_{50}$ at which the surface potential developed before exposure decays to half and exposure $E_{90}$ at which the surface potential developed before exposure decays to one tenth, and residual potential $R_R$ represented by the surface potential at an exposure of 100 μJ/cm².

The results are as follows:

| $V_0$ | +650 V |
|---|---|
| $E_{50}$ | 2.6 μJ/cm² |
| $E_{90}$ | 9.3 μJ/cm² |
| $DD_{10}$ | 74% |
| $V_R$ | +20 V |

COMPARATIVE EXAMPLE A-1

An electrophotographic photoreceptor was prepared in the same manner as in Example A-1 except that the coating solution for photoconducting layer was prepared free of Exemplary Compound (1). The electrophotographic photoreceptor thus prepared was then measured for electric properties in the same manner as in Example A-1.

The results are as follows:

| $V_0$ | +670 V |
|---|---|
| $E_{50}$ | 3.8 μJ/cm² |
| $E_{90}$ | 12.6 μJ/cm² |
| $DD_{10}$ | 75% |
| $V_R$ | +22 V |

EXAMPLE A-2

3.0 parts by weight of an e-type copper phthalocyanine (Liophoton ERPC), 0.3 parts by weight of Exemplary Compound (5), and 3.0 parts by weight of a polyester resin (Vylon 200) were dissolved in 100 parts by weight of tetrahydrofuran. The solution was then subjected to dispersion in a ball mill over 20 minutes. The dispersion thus prepared was then coated on an electrically conductive support (same Al-vacuum deposited film as used in Example A-1) by means of a wire round rod, and dried to obtain a 0.5-μm thick charge-generating layer thereon.

A solution of 9.3 parts by weight of hydrazone compound of the general formula:

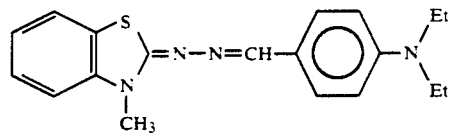

and 10 parts by weight of polycarbonate of bisphenol A in 50 parts by weight of dichloromethane was coated on the charge-generating layer by means of a wire round rod, and dried to form a 20-μm thick charge-transporting layer thereon to prepare the desired electrophotographic photoreceptor. The electrophotographic photoreceptor thus prepared was then measured for electric properties in the same manner as in Example A-1 except that the material was charged at −8 kv.

The results are as follows:

| $V_0$ | −718 V |
|---|---|
| $E_{50}$ | 1.2 μJ/cm² |
| $E_{90}$ | 3.4 μJ/cm² |
| $DD_{10}$ | 77% |
| $V_R$ | −20 V |

Thereafter, the charging and exposure steps were repeated 10,000 times. The specimen was again measured for electric properties. As a result, little or no change was found.

COMPARATIVE EXAMPLE A-2

An electrophotographic photoreceptor was prepared in the same manner as in Example A-2 except that the coating solution for the photoconducting layer was prepared free of Exemplary Compound (5). The electrophotographic photoreceptor thus prepared was then measured for electric properties in the same manner as in Example A-2.

The results are as follows:

| $V_0$ | −738 V |
|---|---|
| $E_{50}$ | 2.0 μJ/cm² |
| $E_{90}$ | 5.8 μJ/cm² |
| $DD_{10}$ | 79% |
| $V_R$ | −24 V |

EXAMPLE A-3

An electrophotographic photoreceptor was prepared in the same manner as in example A-2 except that the ε-type copper phthalocyanine (Liophoton EPRC) was replaced by an X-type metal-free phthalocyanine (Fastogen Blue 8120, available from Dianippon Ink and Chemicals Co., Ltd.). The electrophotographic photoreceptor thus prepared was then measured for electric properties in the same manner as in Example A-2.

The results are as follows:

| $V_0$ | −723 V |
|---|---|
| $E_{50}$ | 0.6 μJ/cm² |
| $E_{90}$ | 1.8 μJ/cm² |
| $DD_{10}$ | 76% |
| $V_R$ | −13 V |

Thereafter, the charging and exposure steps were repeated 10,000 times. The specimen was again measured for electric properties. As a result, little or no change was found.

COMPARATIVE EXAMPLE A-3

An electrophotographic photoreceptor was prepared in the same manner as in Example A-3 except that the coating solution for photoconducting layer was prepared free of Exemplary Compound (5). The electrophotographic photoreceptor thus prepared was then measured for electric properties in the same manner as in Example A-2.

The results are as follows:

| | |
|---|---|
| $V_0$ | −740 V |
| $E_{50}$ | 0.9 μJ/cm$^2$ |
| $E_{90}$ | 2.7 μJ/cm$^2$ |
| $DD_{10}$ | 78% |
| $V_R$ | −15 V |

EXAMPLE A-4

An electrophotographic photoreceptor was prepared in the same manner as in Example A-2 except that the ε-type copper phthalocyanine (Liophoton EPRC) was replaced by an α-type titanyl copper phthalocyanine (Fastogen Blue 8120, available from Dainippon Ink and Chemicals Co., Ltd.). The electrophotographic photoreceptor thus prepared was then measured for electric properties in the same manner as in Example A-2.

The results are as follows:

| | |
|---|---|
| $V_0$ | −710 V |
| $E_{50}$ | 0.35 μJ cm$^2$ |
| $E_{90}$ | 1.0 μJ cm$^2$ |
| $DD_{10}$ | 75% |
| $V_R$ | −10 V |

Thereafter, the charging and exposure steps were repeated 10,000 times. The specimen was again measured for electric properties. As a result, little or no change was found.

COMPARATIVE EXAMPLE A-4

An electrophotographic photoreceptor was prepared in the same manner as in Example A-4 except that the coating solution for photoconducting layer was prepared free of Exemplary Compound (5). The electrophotographic photoreceptor thus prepared was then measured for electric properties in the same manner as in example A-2.

The results are as follows:

| | |
|---|---|
| $V_0$ | −720 V |
| $E_{50}$ | 0.5 μJ/cm$^2$ |
| $E_{90}$ | 1.5 μJ/cm$^2$ |
| $DD_{10}$ | 77% |
| $V_R$ | −11 V |

EXAMPLE A-5–10

An electrophotographic photoreceptor was prepared in the same manner as in Example A-2 except that Exemplary Compound (5) was replaced by the exemplary compounds set forth in Table A-1. The electrophotographic photoreceptor thus prepared was then measured for electric properties in the same manner as in Example A-2. The results are set forth in Table A-1.

TABLE A-1

| Example | Exemplary Compound | $V_0$ (V) | $E_{50}$ (μJ/cm$^2$) | $E_{90}$ (μJ/cm$^2$) | $DD_{10}$ (%) | $V_R$ (V) |
|---|---|---|---|---|---|---|
| A-5 | (3) | −710 | 1.2 | 3.4 | 77 | −22 |
| A-6 | (9) | −704 | 1.4 | 3.8 | 78 | −26 |
| A-7 | (13) | −723 | 1.6 | 4.2 | 80 | −27 |
| A-8 | (18) | −722 | 1.1 | 3.0 | 74 | −20 |
| A-9 | (23) | −700 | 1.5 | 3.8 | 77 | −24 |
| A-10 | (27) | −696 | 1.4 | 3.7 | 74 | −25 |

EXAMPLE A-11

3 parts by weight of an X-type metal-free phthalocyanine (Dainippon Ink and Chemicals, Incorporated) was subjected to dispersion with a solution of 3 parts by weight of a polyester resin (Vylon 200) in 100 parts by weight of chlorobenzene in a ball mill over 20 hours. 0.3 parts by weight of Exemplary Compound (5) was then dissolved in the dispersion. The coating solution thus prepared was then coated on an electrically conductive support by means of a wire round rod, and dried to obtain a 0.5-μm thick charge-generating layer. Thereafter, a charge-transporting layer was provided on the charge-generating layer in the same manner as in Example A-2 to prepare the desired electrophotographic photoreceptor. The electrophotographic photoreceptor thus prepared was then measured for electric properties in the same manner as in Example A-2.

The results are as follows:

| | |
|---|---|
| $V_0$ | −722 V |
| $E_{50}$ | 1.1 μJ/cm$^2$ |
| $E_{90}$ | 3.2 μJ/cm$^2$ |
| $DD_{10}$ | 78% |
| $V_R$ | −22 V |

Thereafter, the charging and exposure steps were repeated 10,000 times. The specimen was again measured for electric properties. As a result, little or no change was found.

Comparison of the results of Example A-1 and Comparative Example A-1, Examples A-2, A-5 to A-10 and Comparative Example A-2, Examples A-3 and A-11 and Comparative Example 3, and Example A-4 and Comparative Example A-4 shows that the electrophotographic photoreceptors. comprising the compound (I) or (II) exhibit a sensitivity 1.5 times to twice higher than the comparative photoreceptors. It is also shown that the electrophotographic photoreceptors of the present invention exhibit little difference in chargeability, decay in a dark place and residual potential from the comparative photoreceptors and thus still exhibit excellent electrophotographic properties. It is also confirmed that the electrophotographic photoreceptors of Examples A-2, A-3, A-4 and A-13 exhibit little or no change in electric properties between the initial values and the values determined after repeated use of 10,000 times.

It can thus be seen that the electrophotographic photoreceptors of the present examples can accomplish the object of the present invention, i.e., high sensitivity and high durability electrophotographic photoreceptor which exhibits a high potential stability and a small residual potential upon repeated use.

EXAMPLE B-1

3.0 parts by weight of an e type copper phthalocyanine (Liophoton ERPC, available from Toyo Ink Manufacturing Co., Ltd.), 0.3 parts by weight of Exemplary Compound (1), 15.0 parts by weight of benzyl methacrylate-methacrylic acid copolymer (monomer composition ratio: 60:40 (molar ratio)), 100 parts by weight of tetrahydrofuran, and 20 parts by weight of cyclohexanone were charged into a 500-ml glass vessel with glass beads. The material was subjected to dispersion by means of a paint shaker (available from Toyo Seiki Seisakusho K.K.) over 120 minutes. The glass beads were then filtered off to obtain a dispersion for a photoconducting layer.

The dispersion for the photoconducting layer was then coated on a 0.25-$\mu$m thick grained aluminum plate, and dried to obtain an electrophotographic printing plate precursor comprising a photoconducting layer having a dried film thickness of 5.0 $\mu$m.

The electrophotographic printing plate precursor thus prepared was then measured for electrophotographic sensitivity by means of EPA-8100 (available from Kawaguchi Denki K.K.) in a static process. In particular, the specimen was corona-charged at +8.0 kv and then exposed to monochromatic light of a wavelength of 780 nm at an intensity of 1 mW/m$^2$. The specimen was examined for electrophotographic properties, i.e., surface potential $V_O$ developed shortly after charging, charge retention $DD_{30}$ represented by the ratio of the surface potential developed 30 seconds after charging to $V_O$, and sensitivity represented by exposure $E_{50}$ at which the surface potential developed before exposure decays to half and exposure $E_{80}$ at which the surface potential developed before exposure decays to one fifth.

The results are as follows:

| | |
|---|---|
| $V_0$ | +454 V |
| $E_{50}$ | 4.9 $\mu$J/cm$^2$ |
| $E_{80}$ | 6.3 $\mu$J/cm$^2$ |
| $DD_{30}$ | 94% |

The specimen was then charged at a surface potential of +450 V in a dark place, and then exposed to light of a wavelength of 780 nm from a semiconductor laser in such a manner that the exposure on the surface of the printing plate reached 5.0 $\mu$J/cm$^2$. The specimen was then developed with a liquid developer prepared by dispersing 5 g of polymethyl methacrylate grain (size: 0.3 $\mu$m) as toner grain in 1 l of Isopar H (available from Esso Standard Co.) and then adding 0.01 g of soybean lecithin as charge adjustor thereto with a bias voltage of 40 V applied between the opposing electrodes. Thus, a sharp positive toner image could be obtained.

The toner image was then fixed at a temperature of 120° C. over 30 seconds. The non-image portions on the electrophotographic printing plate precursor were removed with an etching solution obtained by diluting a mixture of 40 parts by weight of potassium silicate, 10 parts by weight of potassium hydroxide and 100 parts by weight of ethanol with 800 parts by weight of water. The specimen was then thoroughly washed with water, and rubberized to prepare an offset printing plate.

The printing plate thus prepared was then used for printing by means of a Hamada Star 600 CD offset printer in an ordinary process. As a result, 50,000 sheets of remarkably sharp printed matters free of stain on non-image portions could be obtained.

After being stored at a temperature of 35° C. and a relative humidity of 80% over 3 months, the specimen was found to be usable without any problem.

COMPARATIVE EXAMPLE B-1

An electrophotographic printing plate precursor was prepared in the same manner as in Example B-1 except that the coating solution was prepared free of Exemplary Compound (1). The specimen was then measured for electrophotographic properties in the same manner as in Example B-1.

The results are as follows:

| | |
|---|---|
| $V_0$ | +445 V |
| $E_{50}$ | 8.8 $\mu$J/cm$^2$ |
| $E_{80}$ | 10.6 $\mu$J/cm$^2$ |
| $DD_{30}$ | 93% |

The results show that the comparative specimen exhibits a greater induction effect than the specimen of Example B-1 and thus exhibits a poor sensitivity.

COMPARATIVE EXAMPLE B-2

An electrophotographic printing plate precursor was prepared in the same manner as in Example B-1 except that Exemplary Compound (1) was replaced by the following hydrazone compound. The specimen was then measured for electrophotographic properties in the same manner as in Example B-1.

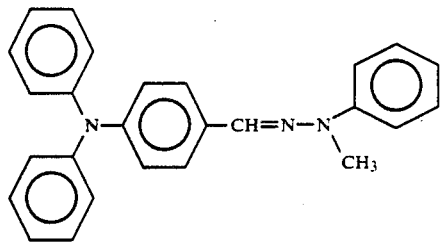

The results are as follows:

| | |
|---|---|
| $V_0$ | +380 V |
| $E_{50}$ | 3.5 $\mu$J/cm$^2$ |
| $E_{80}$ | 12.6 $\mu$J/cm$^2$ |
| $DD_{30}$ | 75% |

The results show that the comparative specimen exhibits poorer chargeability and charge retention than the specimen of Example B-1. It is also shown that the comparative specimen exhibits no induction effect but exhibits a slow decay in surface potential and a low tone reproducibility. Thus, the comparative specimen exhibits a poorer value of $E_{80}$, which is the criterion of practical sensitivity, than the electrophotographic printing plate precursor of Example B-1.

The specimen was then charged at a surface potential of +390 V in a dark place, and exposed to light of a wavelength of 780 nm from a semiconductor laser in such a manner that the exposure on the surface of the printing plate reached 10.0 $\mu$J/cm$^2$.

The specimen was then developed, etched, and used for printing in the same manner as in Example B-1. As a result, a printed matter was obtained with several stains.

After being stored at a temperature of 35° C. and a relative humidity of 80% over 3 months, the specimen was observed having the hydrazone compound as organic photoconducting compound deposited thereon.

FIG. 1 shows the results of the electrophotographic properties of the electrophotographic printing plate precursors of Example B-1 and Comparative Examples B-1 and B-2. (The measurement was effected in accordance with the method as described in Example B-1). Curves (A), (B) and (C) show the decay of surface potential on the electrophotographic printing plate precursors of Example B-1 and Comparative Examples B-1 and B-2, respectively.

In FIG. 1, the curves between −30 seconds and 0 second show dark decay of surface potential while the curves between 0 second and 30 seconds show light decay of surface potential.

FIG. 1 shows that the electrophotographic printing plate precursor of Example B-1 exhibits a lower induction effect that that of Comparative Example B-1 (i.e., the period during which the surface potential hardly decays in the initial stage is shorter). This shows that the incorporation of Exemplary Compound (1) causes no deterioration in chargeability and charge retention and does not impair hard contrast.

The electrophotographic printing plate precursor of Comparative Example B-2 exhibits no induction effect but shows a slow light decay of surface potential and a poorer practical sensitivity than the electrophotographic printing plate precursor of Example B-1. It is also shown that the specimen of Comparative Example B-2 exhibits poorer chargeability and charge retention than the specimen of Example B-1.

EXAMPLES B-2 – B-9

An electrophotographic printing plate precursor was prepared in the same manner as in Example B-1 except that Exemplary Compound (1) was replaced by the compounds as set forth in Table 1, respectively. The electrophotographic printing plate precursor thus prepared was then measured for electrophotographic properties in the same manner as in Example B-1. The results are set forth in Table B-1.

TABLE B-1

| Example | Exemplary Compound | $V_0$ (V) | $DD_{30}$ (%) | $E_{50}$ ($\mu J/cm^2$) | $E_{80}$ ($\mu J/cm^2$) |
|---|---|---|---|---|---|
| B-2 | (2) | 455 | 92 | 5.1 | 6.5 |
| B-3 | (3) | 451 | 93 | 5.2 | 6.6 |
| B-4 | (4) | 446 | 92 | 5.2 | 6.9 |
| B-5 | (10) | 451 | 91 | 5.0 | 6.4 |
| B-6 | (11) | 452 | 91 | 5.3 | 6.6 |
| B-7 | (13) | 440 | 92 | 5.0 | 6.8 |
| B-8 | (18) | 445 | 93 | 4.9 | 6.4 |
| B-9 | (23) | 446 | 93 | 5.5 | 7.0 |

EXAMPLE B-10

An electrophotographic printing plate precursor was prepared in the same manner as in Example B-1 except that as phthalocyanine pigment there was used an X-type metal-free phthalocyanine instead of ε-type copper phthalocyanine. The electrophotographic printing plate precursor thus prepared was then measured for electrophotographic properties in the same manner as in Example B-1.

The results are as follows:

| $V_0$ | +430 V |
|---|---|
| $E_{50}$ | 1.1 $\mu J/cm^2$ |
| $E_{80}$ | 1.3 $\mu J/cm^2$ |
| $DD_{30}$ | 92% |

The specimen was then charged at a surface potential of +450 V in a dark place, and then exposed to light of a wavelength of 780 nm from a semiconductor laser in such a manner that the exposure on the surface of the printing plate reached 2.0 $\mu J/cm^2$. The specimen was then developed, etched and used for printing in the same manner as in Example B-1. As a result, 50,000 sheets of remarkably sharp printed matters free of stain on non-image portions could be obtained. After being stored at a temperature of 35° C. and a relative humidity of 80% over 3 months, the specimen was found to be usable without any problem.

EXAMPLE B-11

An electrophotographic printing plate precursor was prepared in the same manner as in Example B-1 except that as phthalocyanine pigment there was used an X-type metal-free phthalocyanine instead of ε-type copper phthalocyanine and as binder resin there was used vinyl benzoate-crotonic acid copolymer (monomer composition ratio: 60:40 (molar ratio)) instead of benzylester methacrylate-methacrylic acid copolymer. The electro photographic printing plate precursor thus prepared was then measured for electrophotographic properties in the same manner as in Example B-1.

The results are as follows:

| $V_0$ | +425 V |
|---|---|
| $E_{50}$ | 1.2 $\mu J/cm^2$ |
| $E_{80}$ | 1.4 $\mu J/cm^2$ |
| $DD_{30}$ | 91% |

The specimen was then charged at a surface potential of +450 V in a dark place, and then exposed to light of a wavelength of 780 nm from a semiconductor laser in such a manner that the exposure on the surface of the printing plate reached 3.0 $\mu J/cm^2$. The specimen was then developed, etched and used for printing in the same manner as in Example B-1. As a result, 50,000 sheets of remarkably sharp printed matters free of stain on non-image portions could be obtained.

After being stored at a temperature of 35° C. and a relative humidity of 80% over 3 months, the specimen was found to be usable without any problem.

In accordance with the present invention, an electrophotographic printing plate precursor which exhibits a high sensitivity, excellent chargeability, excellent charge retention in a dark place and excellent tone reproducibility and serves as an excellent printing photoreceptor can be obtained. Further, the electrophotographic printing plate precursor of the present invention exhibits an excellent elutability with an etching solution and an excellent age stability.

While the invention has been described in detail and with reference to specific embodiments thereof, it will be apparent to one skilled in the art that various changes and modifications can be made therein without departing from the spirit and scope thereof.

What is claimed is:

1. An electrophotographic photoreceptor for copiers or photoprinters comprising a photoconducting layer provided on an electrically conductive support, wherein said photoconducting layer comprises a phthalocyanine pigment and at least one compound represented by the general formula (I) or (II):

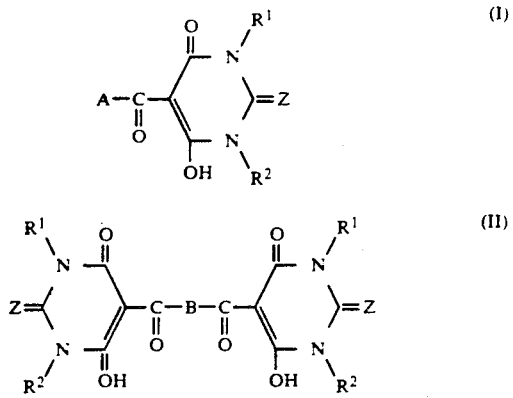

wherein Z represents a sulfur atom or oxygen atom; $R^1$ and $R^2$ may be the same or different and each represents a hydrogen atom, alkyl group, aryl group or aralkyl group; A represents an alkyl group, aryl group, aralkyl group or monovalent heterocyclic group; and B represents an alkylene group, arylene group, polymethylene group or aralkylene group.

2. An electrophotographic photoreceptor as in claim 1, wherein said photoconducting layer comprises a laminated structure comprising a charge-generating layer and a charge-transporting layer, and wherein said charge-generating layer comprises a phthalocyanine pigment and at least one of said compounds represented by general formula (I) or (II).

3. An electrophotographic photoreceptor as in claim 1, wherein the light source for said copier or photoprinter is a laser.

4. An electrophotographic photoreceptor as in claim 3, wherein said phthalocyanine pigment has peak absorption in the wavelength range of 780 to 830 nm.

5. An electrophotographic photoreceptor as in claim 1, wherein substituents for alkyl, aryl or aralkyl groups represented by $R^1$ and $R^2$ are selected form the group consisting of a cyano group, a hydroxy group, a carboxyl group, a nitro group, a halogen atom, an amino group, an alkyl group, an alkoxy group, an aryl group, an aryloxy group, an alkoxycarbonyl group, an acyloxy group, an amino group substituted by an alkyl, aryl or aralkyl group, and a trifluoromethyl group.

6. An electrophotographic photoreceptor as in claim 1, wherein $R^1$ and $R^2$ are selected from the group consisting of straight-chain, branched and substituted alkyl groups, aryl groups, substituted aryl groups, aralkyl groups and substituted aralkyl groups.

7. An electrophotographic photoreceptor as in claim 1, wherein A represents a substituted or unsubstituted alkyl group, a substituted or unsubstituted aryl group, a substituted or unsubstituted aralkyl group, or a monovalent heterocyclic group which may contain substituents, and wherein said substituents are selected from the group consisting of a cyano group, a hydroxy group, a carboxyl group, a nitro group, a halogen atom, an amino group, an alkyl group, an alkoxy group, an aryl group, an aryloxy group, an amino group substituted by an alkyl, aryl or aralkyl group and a trifluoromethyl group.

8. An electrophotographic photoreceptor as in claim 1, wherein the content of the phthaloxyasnine pigment in the electrophotographic light-sensitive layer is in the range of 0.01 to 2 times by weight that of the binder.

9. An electrophotographic photoreceptor as in claim 1, wherein the content of the compound of formula (I) or (II) is in the range of 0.01 to 1 time by weight that of the phthalocyanine pigment.

10. An electrophotographic printing plate precursor which comprises a photoconducting layer containing at least a photoconducting pigment and a binder resin on an electrically conductive support and is adapted to form a printing plate in an electrophotographic process comprising forming a toner image, and then removing said photoconducting layer from the non-image portions, characterized in that said photoconducting pigment is a phthalocyanine pigment and said photoconducting layer further comprises a compound represented by the general formula (I) or (II):

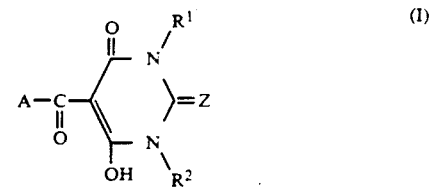

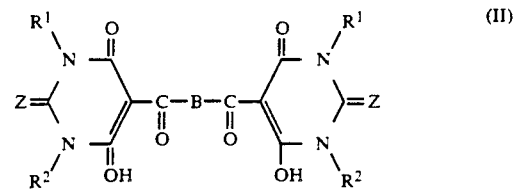

wherein Z represents a sulfur atom or oxygen atom; $R^1$ and $R^2$ may be the same or different and each represents a hydrogen atom, alkyl group, aryl group or aralkyl group; A represents an alkyl group, aryl group or monovalent heterocyclic group; and B represents an alkylene group, arylene group, polymethylene group or aralkylene group.

11. An electrophotographic printing plate precursor as in claim 10, wherein the content of phthalocyanine pigment in the photoconducting layer is in the range of 3 to 50 % by weight based on the solid content in the photoconducting layer.

12. An electrophotographic printing plate precursor as in claim 10, wherein the content of the compound of formulas (I) or (II) is in the range of 1 to 100 % by weight based on the weight of phthalocyanine pigment.

13. An electrophotographic photoreceptor as in claim 10, wherein substituents for alkyl, or aralkyl groups represented by $R^1$ and $R^2$ are selected from the group consisting of a cyano group, a hydroxy group, a carboxyl group, a nitro group, a halogen atom, an amino group, an alkyl group, an alkoxy group, an aryl group, an aryloxy group, an alkoxycarbonyl group, an acyloxy group, an alkyl group, an amino group substituted by an alkyl, aryl or aralkyl group, and a trifluoromethyl group.

14. An electrophotographic photoreceptor as in claim 10, wherein $R^1$ and $R^2$ are selected from the group consisting of straight-chain, branched and substituted alkyl groups, aryl groups, substituted aryl groups, aralkyl groups and substituted aralkyl groups.

15. An electrophotographic photoreceptor as in claim 10, wherein A represents a substituted or unsubstituted alkyl group, a substituted or unsubstituted aryl group, a substituted or unsubstituted aralkyl group, or a monovalent heterocyclic group which may contain substituents, and wherein said substituents are selected from the group consisting of a cyano group, a hydroxy group, a carboxyl group, a nitro group, a halogen atom, an amino group, an alkyl group, an alkoxy group, an aryl group, an aryloxy group, an alkoxycarbonyl group, an amino group substituted by an alkyl, aryl or aralkyl group, and a trifluoromethyl group.

* * * * *